(12) United States Patent
Shields et al.

(10) Patent No.: US 10,028,736 B2
(45) Date of Patent: Jul. 24, 2018

(54) NEEDLE DRIVER

(71) Applicant: Novasurg Innovations, LLC, Cincinnati, OH (US)

(72) Inventors: John Martin Shields, Gainesville, FL (US); Syed M. Hussain, Libertyville, IL (US); Collin James Loch, Cincinnati, OH (US); Nathan Daniel Grubbs, West Chester, OH (US)

(73) Assignee: NOVASURG INNOVATIONS, LLC, Cincinnati, OH (US)

( * ) Notice: Subject to any disclaimer, the term of this patent is extended or adjusted under 35 U.S.C. 154(b) by 309 days.

(21) Appl. No.: 14/853,280

(22) Filed: Sep. 14, 2015

(65) Prior Publication Data

US 2016/0000423 A1  Jan. 7, 2016
US 2016/0331369 A9  Nov. 17, 2016

Related U.S. Application Data

(63) Continuation-in-part of application No. 13/840,459, filed on Mar. 15, 2013, now Pat. No. 9,326,766, and
(Continued)

(51) Int. Cl.
*A61B 17/04* (2006.01)
*A61B 17/062* (2006.01)
(Continued)

(52) U.S. Cl.
CPC ........ *A61B 17/0469* (2013.01); *A61B 17/062* (2013.01); *A61B 17/0482* (2013.01);
(Continued)

(58) Field of Classification Search
CPC ............ A61B 17/0469; A61B 17/0482; A61B 17/062; A61B 17/29; A61B 17/2909;
(Continued)

(56) References Cited

U.S. PATENT DOCUMENTS 532,306 A  1/1895  Brown
2,652,832 A  9/1953  Castroviejo
(Continued)

FOREIGN PATENT DOCUMENTS

EP  0571057 A1  11/1993

OTHER PUBLICATIONS

International Search Report and Written Opinion dated Oct. 10, 2014 for corresponding International Application Serial No. PCT/US2014/27955, filed Mar. 14, 2014 (13 pages).
(Continued)

*Primary Examiner* — Robert Lynch
(74) *Attorney, Agent, or Firm* — Daniel F. Nesbitt; Hasse & Nesbitt LLC

(57) ABSTRACT

A needle driver includes a first elongated body that defines an interior chamber. A second elongated body defines an interior space, and is slideable within the interior chamber defined by the first elongated body between a retracted position and an extended position. The needle driver also includes a clamping device having a clamping end and a connecting member, which is affixed to the first elongated body and coupled within the clamping end. A biasing shaft is slideably disposed within the interior space defined by the second elongated body. An actuator is affixed to the biasing shaft and is slideable in a proximal direction and a distal direction.

28 Claims, 25 Drawing Sheets

Related U.S. Application Data a continuation-in-part of application No. PCT/US2014/027955, filed on Mar. 14, 2014.

(51) Int. Cl.
    *A61B 17/29* (2006.01)
    *A61B 17/30* (2006.01)

(52) U.S. Cl.
    CPC .......... *A61B 17/29* (2013.01); *A61B 17/2909* (2013.01); *A61B 2017/2937* (2013.01); *A61B 2017/2946* (2013.01); *A61B 2017/305* (2013.01)

(58) Field of Classification Search
    CPC .... A61B 2017/2908; A61B 2017/2913; A61B 2017/2915; A61B 2017/2916; A61B 2017/2917; A61B 2017/2923; A61B 2017/2933; A61B 2017/2934; A61B 2017/2936; A61B 2017/2937; A61B 2017/2946
    See application file for complete search history.

(56) References Cited

U.S. PATENT DOCUMENTS

| | | | |
|---|---|---|---|
| 3,834,021 A | 9/1974 | White et al. | |
| 4,165,745 A | 8/1979 | Heifetz | |
| 4,345,601 A | 8/1982 | Fukuda | |
| 4,446,866 A | 5/1984 | Davison | |
| 4,491,135 A | 1/1985 | Klein | |
| 4,655,219 A * | 4/1987 | Petruzzi ................. | A61B 1/018 606/206 |
| 4,760,848 A | 8/1988 | Hasson | |
| 4,994,079 A | 2/1991 | Genese et al. | |
| 5,129,912 A | 7/1992 | Noda et al. | |
| 5,338,317 A | 8/1994 | Hasson et al. | |
| 5,405,353 A | 4/1995 | Randall | |
| 5,425,705 A | 6/1995 | Evard et al. | |
| 5,499,997 A | 3/1996 | Sharpe et al. | |
| 5,628,757 A | 5/1997 | Hasson | |
| 5,653,717 A | 8/1997 | Ko et al. | |
| 5,826,928 A * | 10/1998 | Shang ...................... | B25B 9/00 294/100 |
| 5,851,211 A | 12/1998 | Khoury | |
| 5,944,739 A | 8/1999 | Zlock et al. | |
| 5,951,575 A | 9/1999 | Bolduc et al. | |
| 5,954,733 A | 9/1999 | Yoon | |
| 6,077,278 A | 6/2000 | Mayer | |
| 6,090,129 A | 7/2000 | Ouchi | |
| 6,102,920 A | 8/2000 | Sullivan et al. | |
| 6,149,642 A | 11/2000 | Gerhart et al. | |
| 6,361,540 B1 * | 3/2002 | Gauderer ............. | A61B 17/221 606/106 |
| 7,137,988 B2 | 11/2006 | Frye | |
| 8,252,021 B2 | 8/2012 | Boulnois et al. | |
| 8,821,444 B2 | 9/2014 | Scheller et al. | |
| 2009/0157098 A1 | 6/2009 | Meybodi | |
| 2011/0106111 A1 | 5/2011 | Yang et al. | |
| 2012/0059394 A1 | 3/2012 | Brenner et al. | |
| 2012/0143223 A1 | 6/2012 | Woodard, Jr. et al. | |
| 2012/0245601 A1 | 9/2012 | Benson | |
| 2012/0289975 A1 | 11/2012 | Martin et al. | |
| 2013/0085326 A1 | 4/2013 | Scheller et al. | |
| 2014/0276978 A1 | 9/2014 | Shields et al. | |
| 2014/0343528 A1 | 11/2014 | Scheller | |

OTHER PUBLICATIONS

Extended European Search Report dated Feb. 17, 2017 for corresponding European Patent Application No. 14762299.7 (pub. as EP2967546). filed Mar. 14, 2014 (8 pages).

* cited by examiner

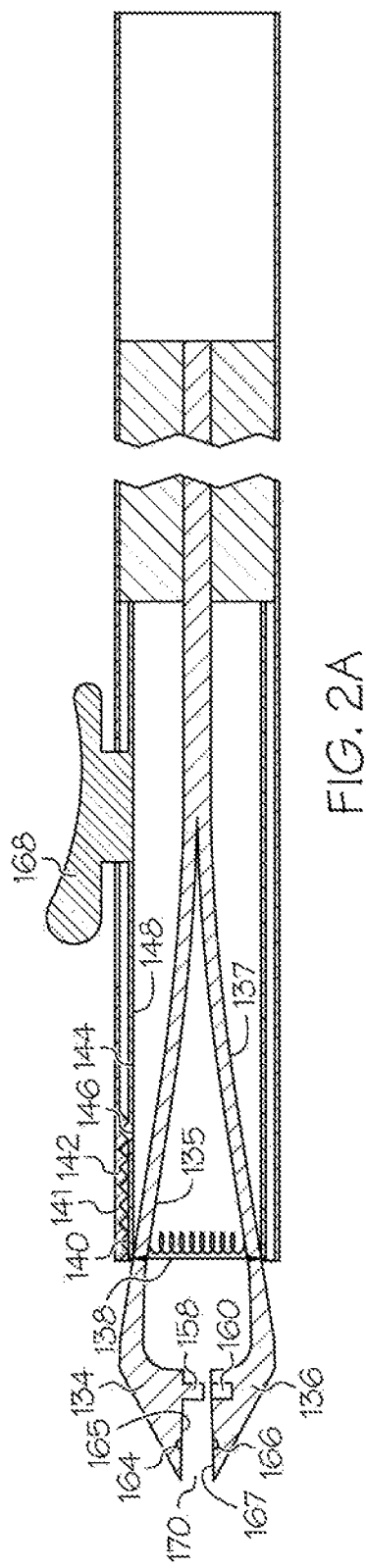
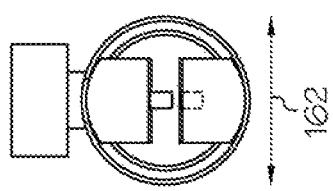
FIG. 2A
FIG. 2B

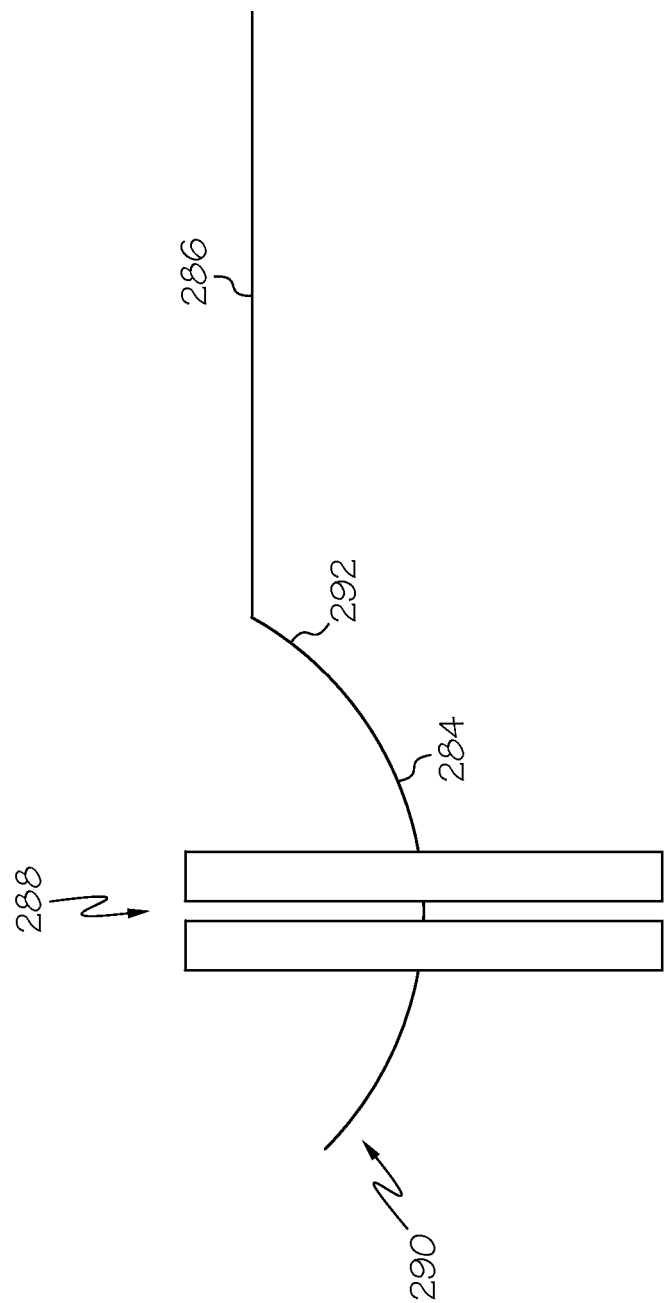

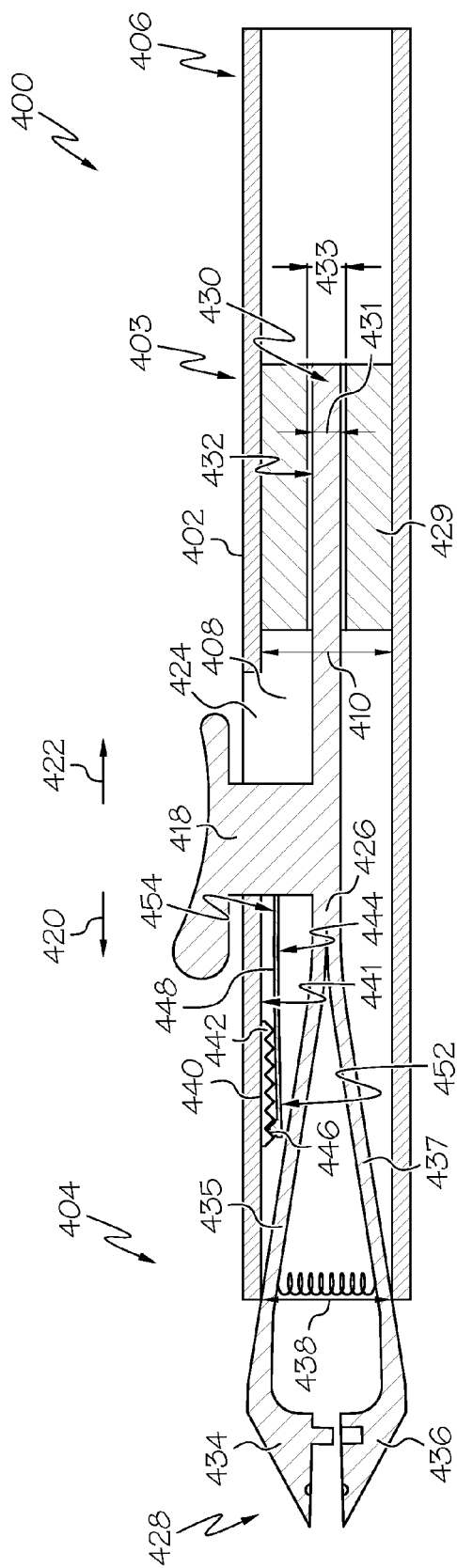
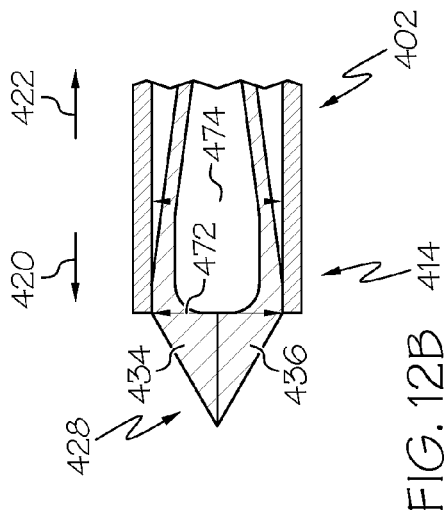
FIG. 12A
FIG. 12B

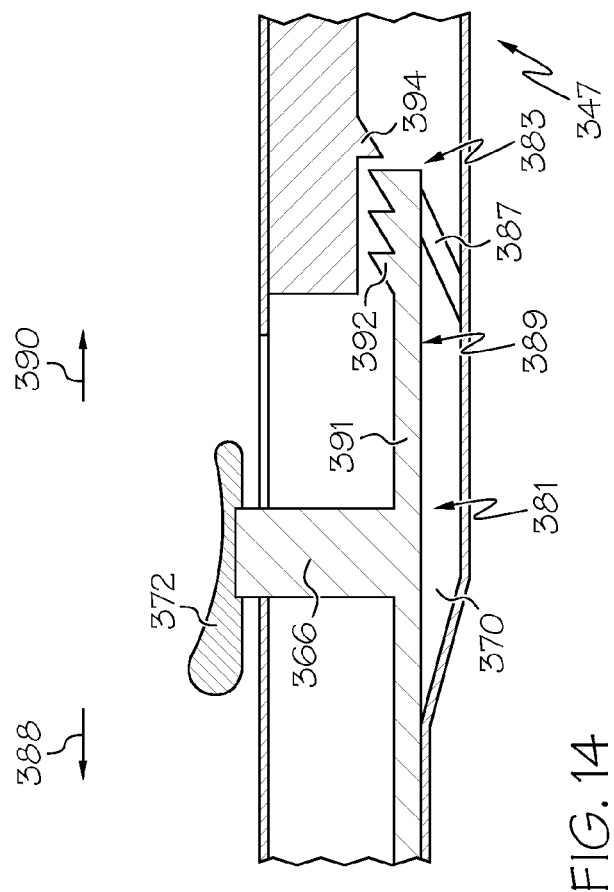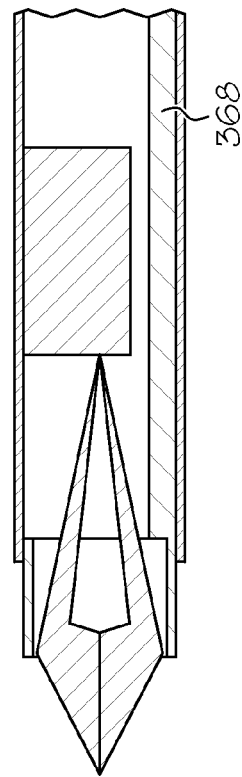
FIG. 14

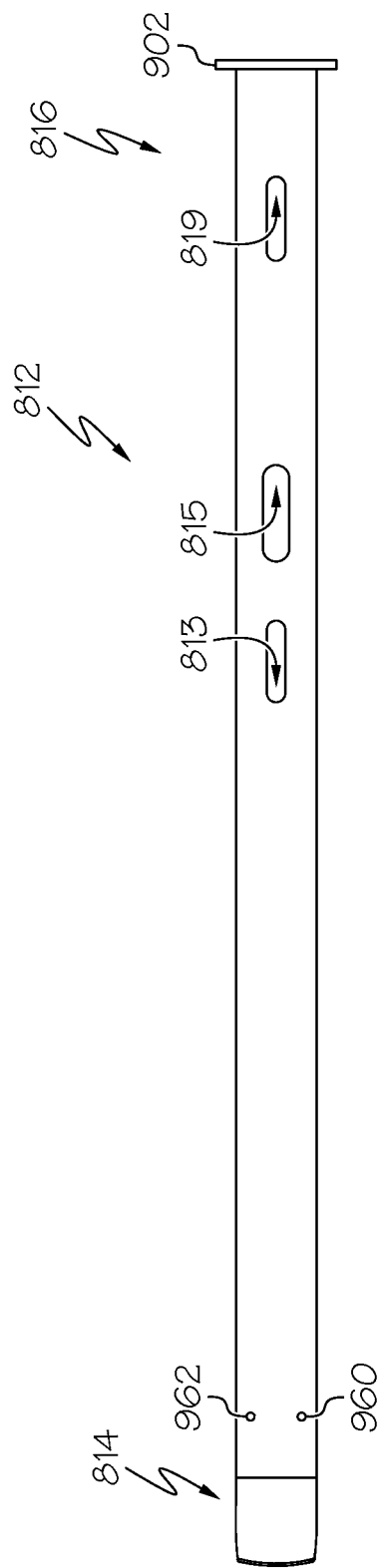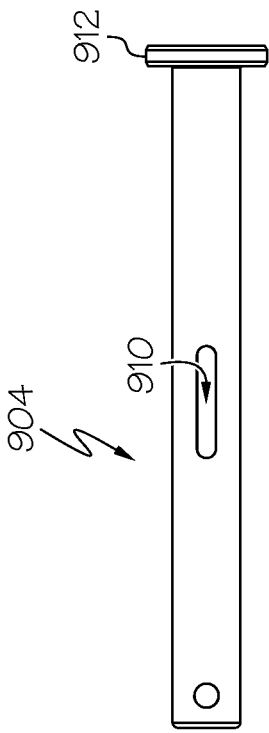

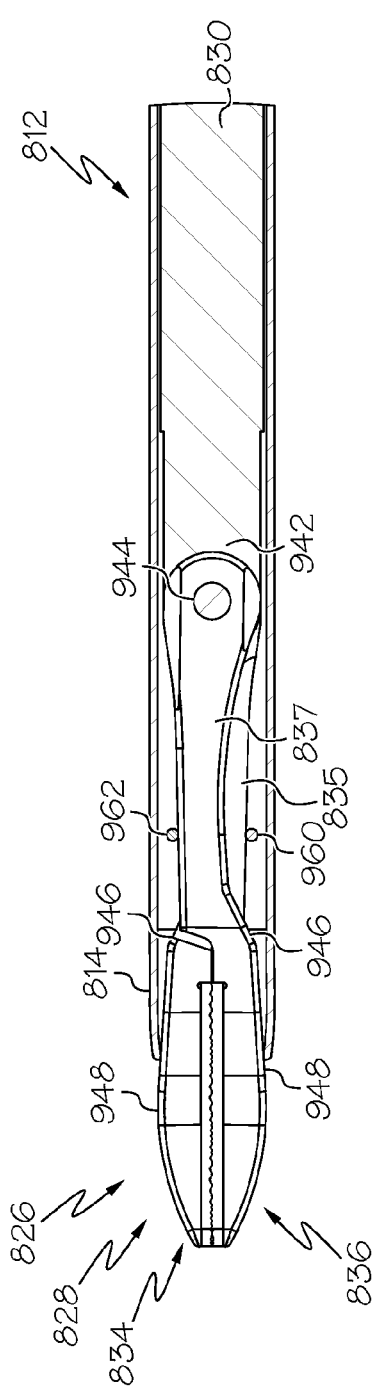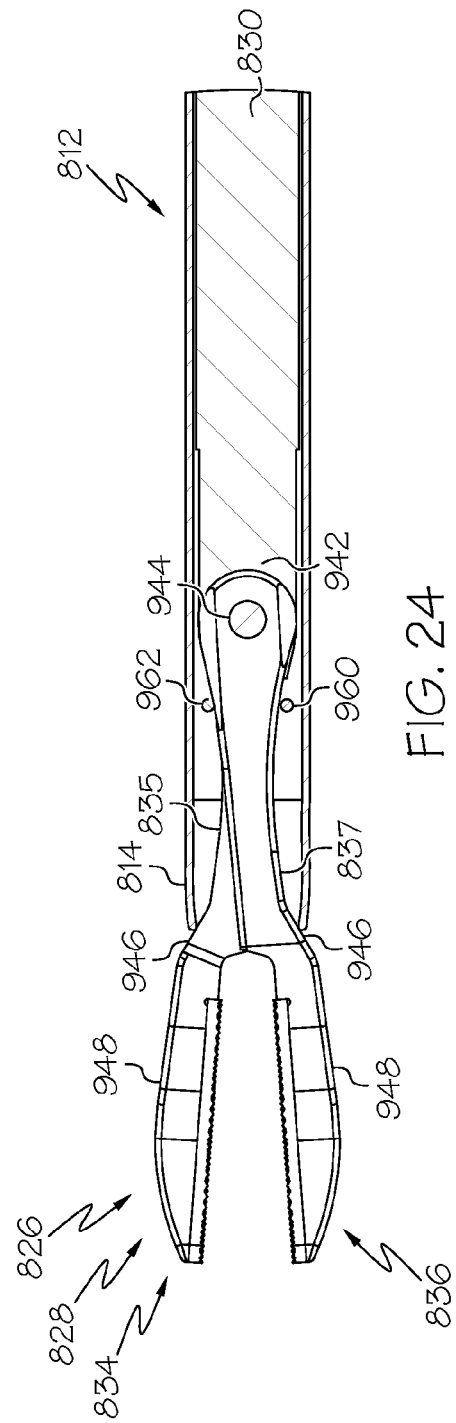

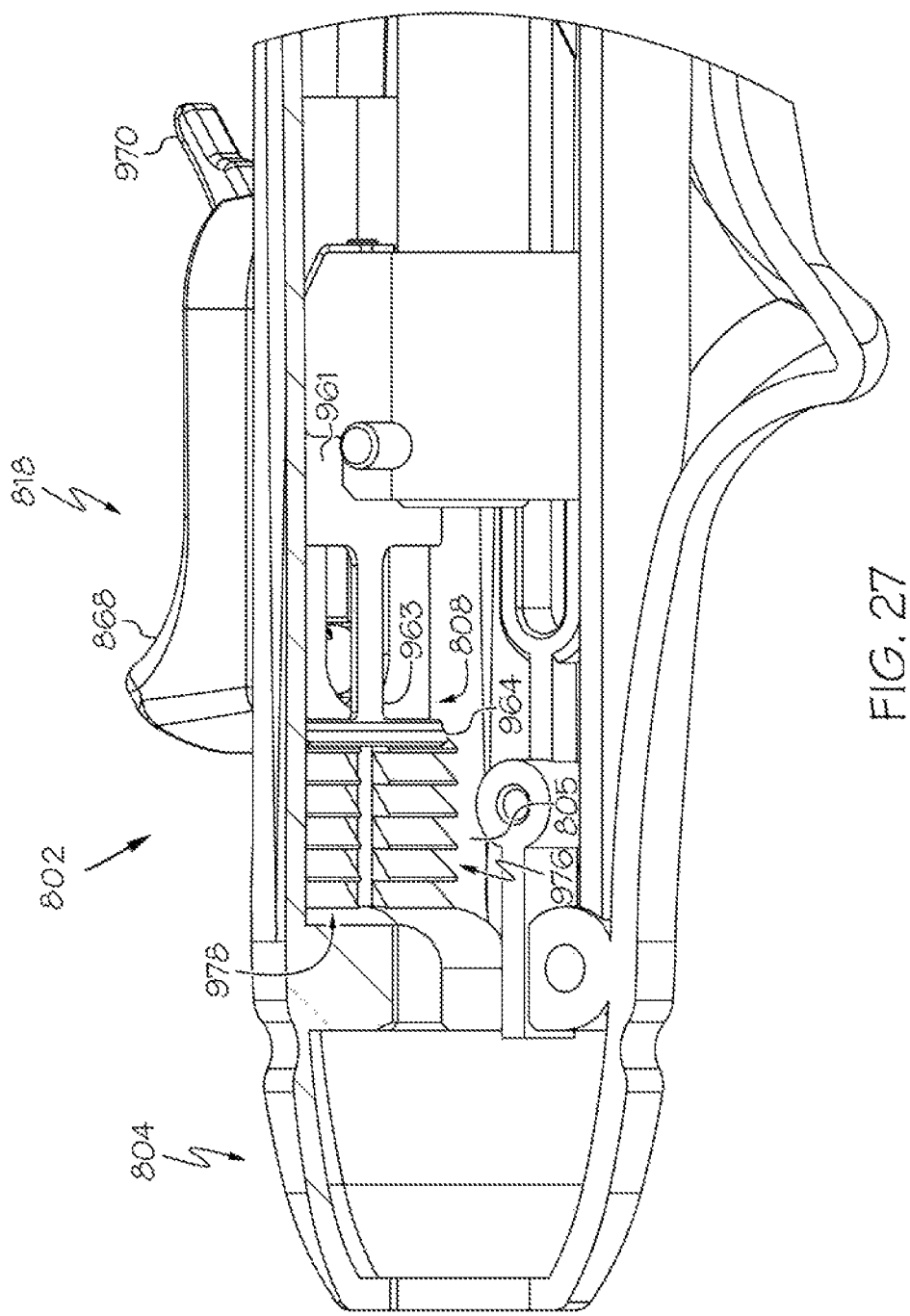

NEEDLE DRIVER

CROSS-REFERENCE TO RELATED APPLICATIONS

This application is a continuation-in-part of U.S. application Ser. No. 13/840,459, filed Mar. 15, 2013 (pending), and International Application No. PCT/US14/27955, filed Mar. 14, 2014 (pending), and hereby expressly incorporates by reference herein the entire disclosures of both of these prior applications.

TECHNICAL FIELD

This invention relates to a needle driver with a clamping device. Specifically, this invention relates to a needle driver having a slideable actuator to operate the clamping device.

BACKGROUND

Suturing is commonly known as the practice of using lengths of medical suture material to ligate or approximate tissue for proper healing after a surgical or other type of invasive medical procedure involving an incision. The process of suturing bodily tissue upon completion of a medical procedure, whether the particular procedure is open, endoscopic, laparoscopic, or another type of procedure, generally encompasses a substantial portion of the respective procedure time. In open-type surgical procedures, which refers to a procedure wherein the surgeon gains access to a surgical site via a relatively large incision, for example, the sutures required to properly ligate such an incision can easily take tens of minutes to properly and carefully apply. In endoscopic and/or laparoscopic type procedures, which generally refers to minimally invasive-type surgical procedures wherein the surgeon gains access to the surgical site via one or more small tissue portals/incisions, the suturing processes may be substantially more complicated, as the surgeon generally has a diminished view of an internal suturing site as well as a substantially reduced physical space for manipulating the respective suturing equipment. Therefore, the time required to suture in these internal-type situations is generally substantially longer than in open-type procedures, in addition to being substantially more difficult for the surgeon to accomplish.

In conventional medical techniques, suturing processes have generally been accomplished with the use of a sharp suture needle carrying a length of suture material, wherein the suture needle is caused to penetrate and pass through the tissue while simultaneously pulling the suture material therethrough. Once the suture material has been pulled through the tissue, the surgeon ties a knot in the suture material and secures the suture. Conventional needle drivers require the surgeon to grip the needle with the jaw portion of the needle driver, possibly locking jaws in tension with a ratchet mechanism in the handle portion, and thereafter, manipulate the needle so as to create sutures. The surgeon may engage and control the needle driver via placement of the appropriate fingers within the respective handle finger holes.

However, a surgeon's manipulation of the conventional needle driver is limited by the physical configuration of the conventional needle driver. For example, as a result of the surgeon having at least one finger placed in the finger holes, the surgeon's ability to manipulate/rotate the needle driver about a longitudinal axis of the needle driver is limited. As such, movements often require the surgeon to go through odd and/or uncomfortable motions, such as elevation of the surgeon's elbow corresponding to the hand having the needle driver therein upward in order to engage tissue with the needle. This process is known to cause strain and fatigue on a surgeon during suturing, and therefore, presents a potential for fatigue and/or strain based error. Additionally, the configuration of the jaws of conventional needle drivers results in the optimal gripping force being obtained when the jaws of the needle driver are completely closed. Inasmuch as a needle may not be gripped by the needle driver when the jaws are closed, as there is no physical space between the jaws in this position, conventional devices are not capable of gripping the needle with the optimal force available from the respective driver.

The shortcomings of conventional needle drivers are exacerbated when used in connection with microsurgery and endoscopic surgery, as these types of procedures require additional time and surgical effort to complete as a result of the nature of the surgical procedures. This can unduly prolong the duration of surgery, and therefore, prolong the period in which the patient is under anesthesia, which is undesired. Further, as a result of the less than optimal needle gripping force available from conventional devices, surgeons often have difficulty in maintaining a suture needle within the jaws of conventional devices, which may result in dropping a needle. Nevertheless, endoscopic surgery is often preferred over open surgery due to the ability to reduce incision trauma and facilitate wound healing, which directly results in cost savings associated with shorter hospital stays and performing surgery in non-hospital and/or out-patient surgery sites.

There exists a need for a needle driver that provides improved ergonomic characteristics over conventional devices so that the needle driver may be easily manipulated by the surgeon with minimal stress and/or fatigue.

SUMMARY

According to one embodiment, a needle driver includes a first elongated body having a distal end and a proximal end, and defining an interior chamber. The needle driver also includes a second elongated body having a distal end and a proximal end, and defining an interior space. The second elongated body is slideable within the interior chamber defined by the first elongated body, between a retracted position and an extended position. The needle driver further includes a clamping device, a biasing shaft, an actuator and a proximal biasing member. The clamping device includes a clamping end and a connecting member, which is affixed to the first elongated body and coupled with the clamping end. The biasing shaft is slideably disposed within the interior space defined by the second elongated body. The actuator is affixed to the biasing shaft and is slideable in a proximal direction and a distal direction. The proximal biasing member extends between the biasing shaft and the second elongated body.

According to another embodiment, a needle driver includes a first elongated body having a distal end and a proximal end, and defining an interior chamber. The needle driver also includes a second elongated body having a distal end and a proximal end, and defining an interior space. The second elongated body is slideable within the interior chamber defined by the first elongated body, between a retracted position and an extended position. The needle driver further includes a clamping device, a biasing shaft, an actuator, a first cam member and a second cam member. The clamping device includes a first jaw member, a second jaw member, a first arm, a second arm, and a connecting member, the connecting member being affixed to the first elongated body. The biasing shaft is slideably disposed within the interior space defined by the second elongated body. The actuator is affixed to the biasing shaft, and is slideable in a proximal direction and a distal direction. Each of the first cam member and the second cam member is secured to the second elongated body and extends into the interior space defined by the second elongated body. The first arm of the clamping device pivotally couples the first jaw member with the connecting member, and the second arm pivotally couples the second jaw member with the connecting member. The first cam member contacts the first arm as the second elongated body is retracted, biasing the first jaw member toward the open position. The second cam member contacts the second arm as the second elongated body is retracted, biasing the second jaw member toward the open position.

According to yet another embodiment, a needle driver includes a first elongated body having a distal end and a proximal end, and defining an interior chamber. The needle driver also includes a second elongated body having a distal end and a proximal end, and defining an interior space. The second elongated body is slideable within the interior chamber defined by the first elongated body, between a retracted position and an extended position. The needle driver further includes a clamping device, a biasing shaft, an actuator, a proximal biasing member, a locking device, and a lock release member. The clamping device includes a clamping end and a connecting member. The connecting member is affixed to the first elongated body and coupled with the clamping end. The biasing shaft is slideably disposed within the interior space defined by the second elongated body. The actuator is affixed to the biasing shaft, and is slideable in a proximal direction and a distal direction. The proximal biasing member extends between the biasing shaft and the second elongated body. The locking device is attached to the actuator, and is movable with the actuator proximally and distally. The lock release member is coupled with the actuator. The first elongated body includes at least a first plurality of ratchet teeth extending inwardly from the distal end of the first elongated body into the interior chamber defined by the first elongated body, and the locking device is configured for selective engagement with the first plurality of ratchet teeth to releasably lock the actuator. The lock release member is operable for selectively disengaging the locking device from the first plurality of ratchet teeth.

BRIEF DESCRIPTION OF THE DRAWINGS

FIG. 2A is a section view of the needle driver of FIG. 1 with the jaws in the open position.

FIG. 2B is an end view of the needle driver of FIG. 1 with the jaws in the open position.

FIG. 11 is a side section view of a needle suturing tissue.

FIG. 12A is a section view of another embodiment of a needle driver of the invention.

FIG. 12B is a partial sectional view of a first end of the needle driver of FIG. 12A with the jaws in the clamping position.

FIG. 14 is a section view of another embodiment of a needle driver of the invention.

FIG. 20 is an elevational view of a second elongated body of the needle driver of FIG. 16.

FIG. 21 is an elevational view of a biasing shaft of the needle driver of FIG. 16.

FIG. 23 is a fragmentary cross-sectional view depicting a portion of the second elongated body and a portion of the clamping device of the needle driver of FIG. 16, with the clamping end of the clamping device being depicted in the closed position.

FIG. 24 is a fragmentary cross-sectional view similar to FIG. 23, but with the clamping end of the clamping device being depicted in the open position.

FIG. 27 is a fragmentary bottom perspective view depicting an actuator and a portion of the first elongated body of the needle driver, with a distal tooth of the locking device of FIGS. 25 and 26 engaged with individual ones of first and second pluralities of ratchet teeth of the first elongated body.

DETAILED DESCRIPTION

Figure 1:
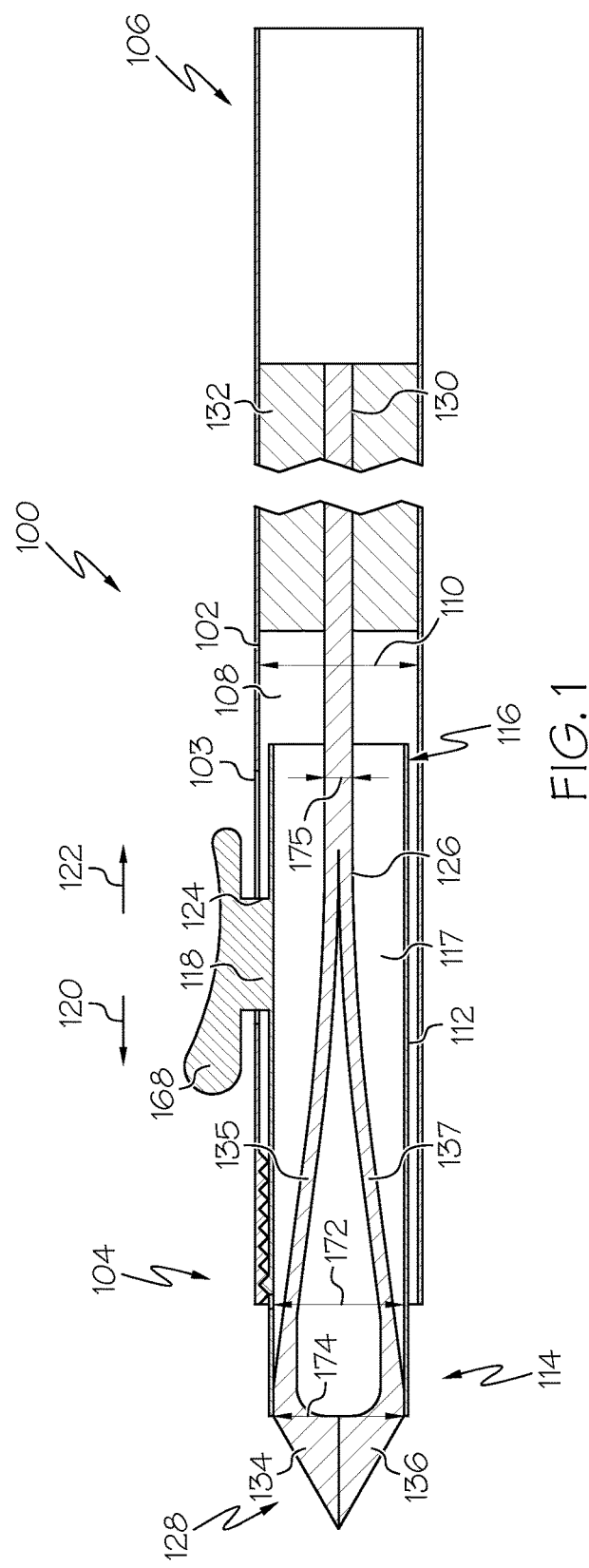
FIG. 1 is a section view of a needle driver of the invention with the jaws in the closed position.

FIG. 1 shows one embodiment of a needle driver 100 of the invention. The needle driver has a first elongated body 102 having a first end 104 and a second end 106. At least a portion of the first elongated body has a substantially hollow interior portion 108 defined by an interior dimension 110. An outer surface 103 of the first elongated body may be knurled to allow the user to maintain a positive grip on the needle driver. Slideably disposed in the first elongated body 102 is a second elongated body 112 having a first end 114, a second end 116, and a substantially hollow interior portion 117. An actuator 118 is affixed to the second elongated body for moving the second elongated body forward and backward in the direction of arrows 120 and 122, respectively. The actuator passes through a slot 124 in the first elongated body 102, which allows the actuator to slide forward and backward in the directions of arrows 120 and 122 respectively. A digit receiver 168 designed for receiving a thumb, index finger, or other digit of the user may be affixed to the actuator 118.

At least partially disposed in the second elongated body is a clamping device 126 having a clamping end 128 and a connecting end 130. The connecting end 130 of the clamping device 126 is affixed to the inside of the first elongated body 102 with a connector 132. The clamping end 128 of the clamping device has a first jaw member 134 and a second jaw member 136 opposing the first jaw member 134. First arm 135 and second arm 137 connect the connected end to the first jaw member and second jaw member. The arms taper from a larger external dimension 174 to a smaller external dimension 175 between the clamping end and the connecting end.

Typically, the first jaw member and the second jaw member are biased away from each other when they are in the relaxed position, as shown in FIG. 2A. Various methods can be used to bias the first and second jaw members away from each other. For example, the material used to make the clamping device may be a spring steel that will allow the first and second jaws to flex inward and outward. Alternatively, a spring 138 may be disposed between the first arm 135 and the second arm 137.

As shown in FIG. 1, an internal dimension 172 of the first end 114 of the second elongated body is approximately the same as an external dimension 174 of the first and second jaw members when the jaw members are in a closed position. As such, when the second elongated body is in a most forward position after being pushed in the direction of arrow 120, it biases the first jaw member and the second jaw member towards each other, causing the jaw members to move towards each other and clamp. When the actuator is moved in the direction of arrow 122, the second elongated body slides in the direction of arrow 122 and away from the clamping end 128. Because of the taper in the arms between the clamping end and the connecting end, the first and second jaw members bias away from each other as the second elongated body 112 is retracted in the direction of arrow 122.

Figure 3:
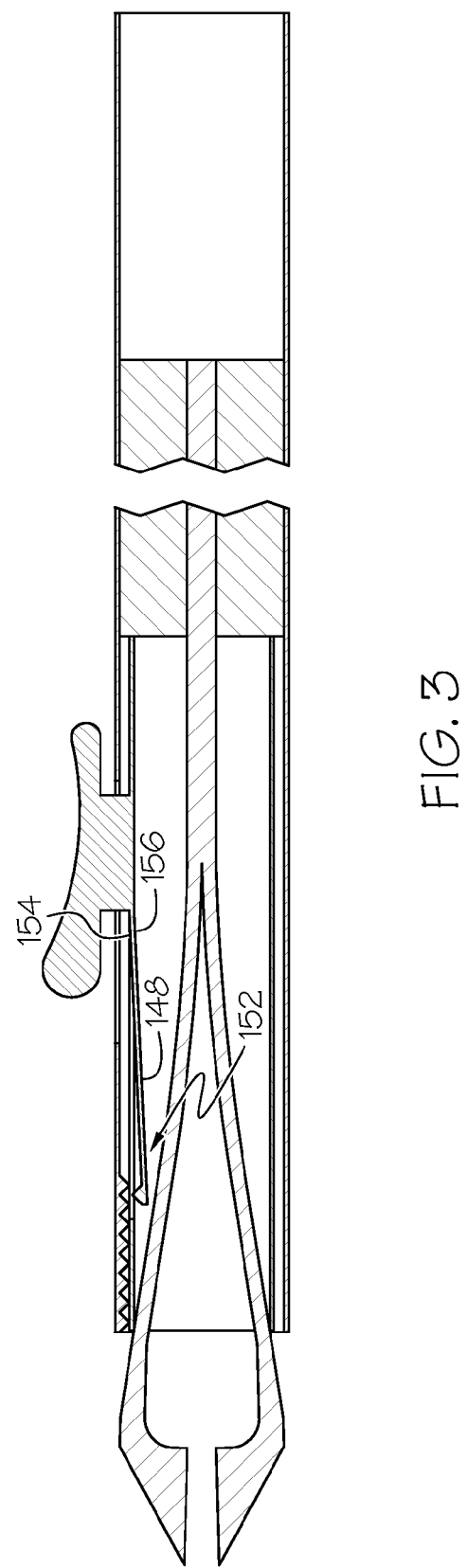
FIG. 3 is a section view of the needle driver of FIG. 1 with the lock in an unlocked position.

A serrated edge 140 having teeth 142 is disposed on an interior portion 141 of the first end 104 of the first elongated body 102. Affixed to the actuator 118 is a locking device 144 with a tooth 146 that mates with the teeth 142 disposed in the first end 104 of the first elongated body 102. Here, the locking device 144 is a flexible bar 148 with a tooth 146 on a distal end 152 of the flexible bar 148. As shown in FIG. 3, a proximal end 154 of the flexible bar 148 is affixed to an interior portion 156 of the second elongated body 112 and connects the tooth 146 with the second elongated body 112. Alternatively, there may be a single tooth disposed on the interior portion 141 of the first elongated body and multiple teeth disposed on the distal end 152 of the flexible bar 148.

Figure 4:
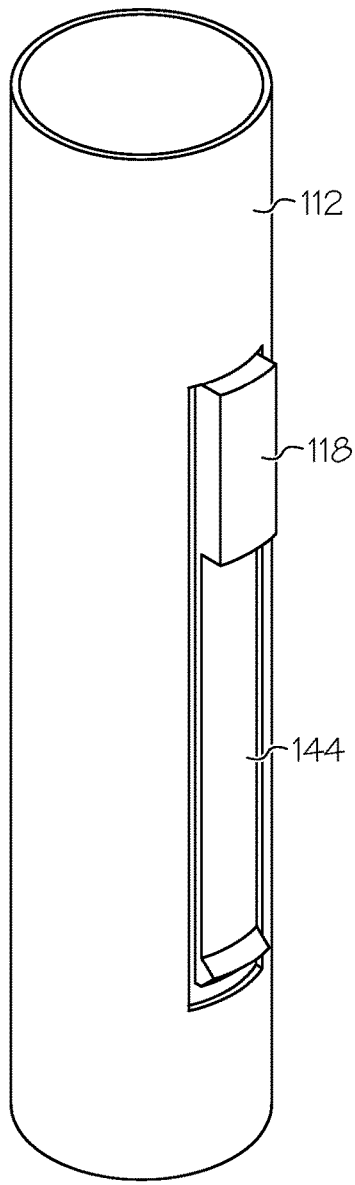
FIG. 4 is a top view of one embodiment of a second elongated body of the invention.
Figure 5:
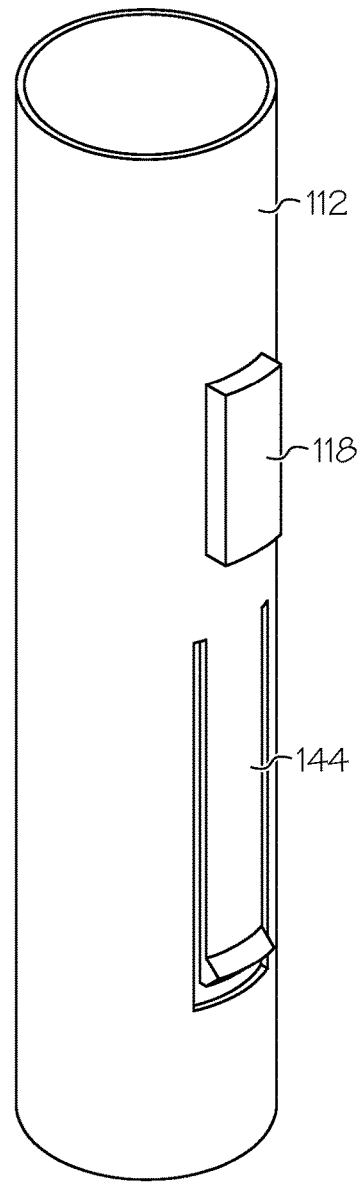
FIG. 5 is a top view of another embodiment of a second elongated body of the invention.

Alternatively, the locking device 144 may be stamped or otherwise formed from the second elongated body 112, as shown in FIG. 4. In this example, the second elongated body is made from a material, such as spring steel, that is resilient and flexible. The actuator 118 is mounted to the flexible bar 148 of the locking device. By pressing down on the actuator, the operator disengages the tooth 146 of the flexible bar 144 from the teeth 142 located on the interior portion of the first elongated body 102. Alternatively, the flexible bar may not be cut back as far as the actuator, as shown in FIG. 5. In the embodiment of FIG. 5, the flexible bar does not extend back to the actuator. In this situation, the tension of the flexible bar and the engagement of its tooth with the teeth of the interior portion of the first elongated body are overcome when the operator slides the actuator in the direction of arrow 122 in FIG. 1. The actuator 118 shown in FIGS. 4 and 5 may also have a digit receiver as shown in FIG. 2A.

As shown in FIG. 2A, the first jaw member 134 may have a pin 158 that aligns with a hole 160 having a diameter sized to receive the pin 158 and located in the second jaw member 136. The pin and hole align the jaws in the lateral direction, represented by arrow 162 in FIG. 2B, so that the jaws do not slide apart in the lateral direction when grasping an item. Alternatively, the second jaw member 136 may have the pin and the first jaw member 134 may have the hole for receiving the pin.

The jaws may also have a relief for receiving a tool such as a needle. As shown in FIG. 2A, the first jaw 134 has a relief 164 on gripping portion 165 and the second jaw 136 has a relief 166 on a gripping portion 167. Typically, the reliefs are sized to fit the intended tool, such as a needle and are cut in a shape to match the tool. For example, if the jaws were made to hold a round needle, the relief 164 would be a semicircle and the relief 166 would be a semicircle. Alternatively, only one jaw may have a relief for grasping a tool and the other jaw may not have a relief. In addition, the gripping portions 165 and 167 of the jaws may be knurled or grated to improve gripping performance. The knurling or grating may be in addition to the reliefs. While the jaws described here are typically used for holding needles, other types of jaws may also be used when required to grasp other tools, instruments, materials or tissue. For example, blunt jaws may be used when the operator desires to grab or manipulate tissue and minimize tissue damage.

In operation, a user holds the first elongated body in a hand with a digit on the digit receiver 168. To open the closed jaws shown in FIG. 1, the user slides the digit receiver in the direction of arrow 122, thereby sliding the second elongated body 112 in the direction of arrow 122. The tension in the arms 135 and 137, or the spring 138, which bias the first jaw member and second jaw member away from each other, causes the first and second jaw members to separate thereby creating a gap 170 between them. The user then inserts a tool, such as a needle for suturing, between the first jaw member and the second jaw member and moves the actuator 118 with the digit receiver 168 in the direction of arrow 120 to clamp the tool between the first and second jaws.

As the actuator 118 is moved in the direction of arrow 120, the tooth 146 on the flexible arm 148 engages with the teeth 142 on the serrated edge 140 located on the interior portion 141 of the first end 104 of the first elongated body 102. The actuator can be locked in a predetermined number of positions depending on where the tooth 146 aligns with the teeth of the serrated edge. In this manner, the user can adjust the clamping force on the tool and can grasp, secure, and lock tools of a varying size between the first and second jaws.

After locking the needle between the jaws, the user can easily manipulate the needle driver by rolling it between his fingers, with the knurled surface of the first elongated body providing a positive grip surface and reducing slippage between the needle driver and the user's fingers. While the first elongated body is typically cylindrical, it could also be multi-sided, such as square, hexagonal, or octagonal. Various shapes could be provided, depending on the users' preferences.

FIG. 11 shows a needle 284 with suture thread 286 being used to suture tissue 288. The needle 284 has a forward end 290 and a rearward end 292. Once the rearward end 292 of the needle is locked in the jaws, the user typically proceeds with suturing by driving the needle through the tissue with the needle driver. Once the needle passes through and the forward end of the needle is exposed on the far side of the tissue, the user releases the needle from the needle driver by pushing down on the actuator to disengage the tooth 146 from the serrated edge 140 and sliding the actuator back in the direction of arrow 122, or by sliding the actuator in the direction of arrow 122 and allowing the tooth 146 to ratchet over the serrated edge 140. The user then grabs the forward end 290 of the needle with the needle driver, locks the jaws on the forward end of the needle, and pulls the needle through the tissue. To ready the needle for the next suture, the needle is released from the needle driver and is then grasped by the needle driver at the rearward end of the needle. The needle is then driven through the tissue and the process is repeated.

Figure 6:
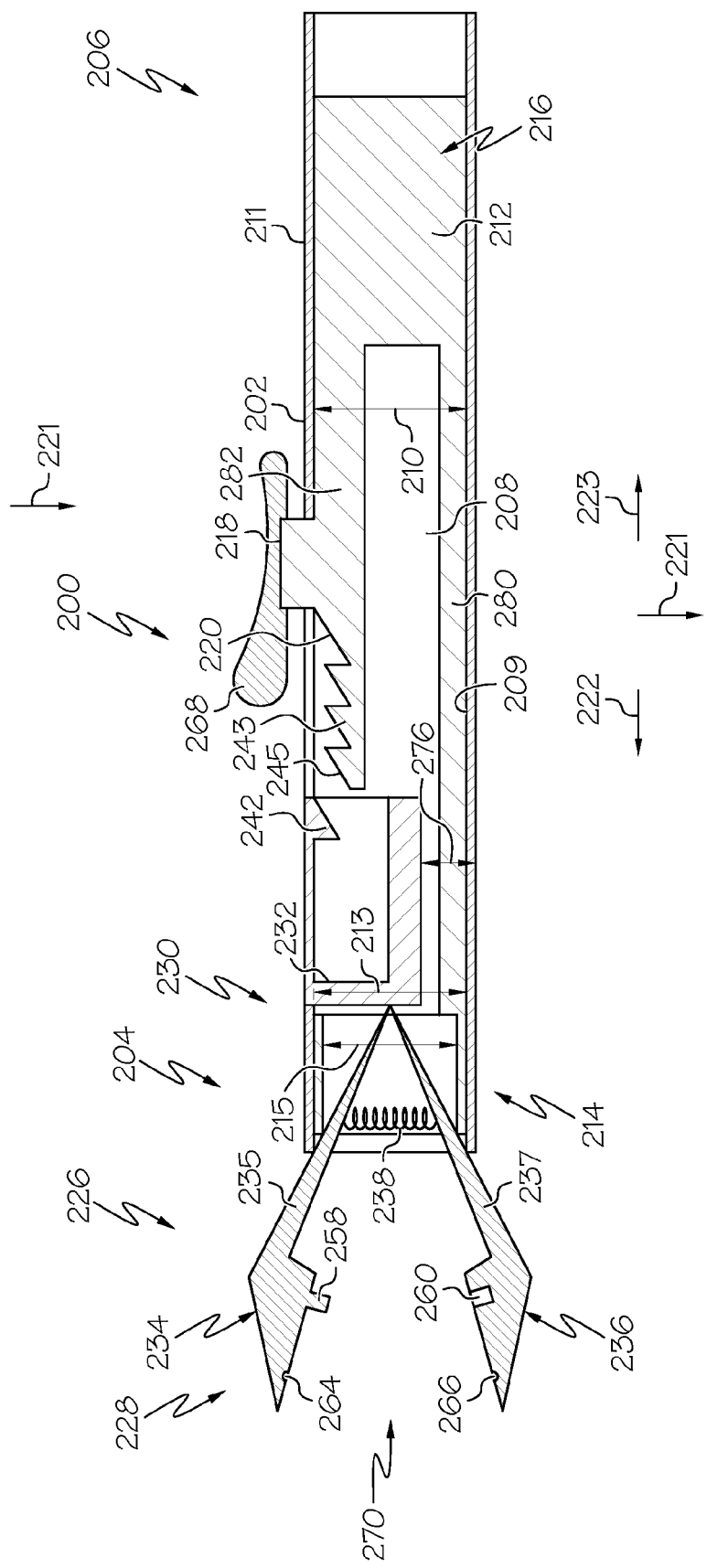
FIG. 6 is a section view of another needle driver of the invention with the jaws in the open position.

FIG. 6 shows another embodiment of a needle driver 200. The needle driver 200 has a first elongated body 202 having a first end 204 and a second end 206. At least a portion of the first elongated body 202 has a substantially hollow interior portion 208 defined by an interior dimension 210. As before, an outer surface 211 of the first elongated body 202 may be knurled to allow the user to maintain a positive grip on the needle driver.

At least partially disposed in the substantially hollow portion of the first elongated body 202 is a second elongated body 212 having a first end 214, a second end 216, and an actuating mechanism 218 and a locking device 220 disposed therebetween. The first end 214 of the second elongated body 212 includes a substantially hollow interior portion with an external dimension 213 slightly less than the internal dimension 210 of the first elongated member and an internal dimension 215 sized to slide over and operate a clamping device 226. A bar 280 connects the first end 214 of the second elongated body 212 to the second end 216 of the second elongated body. The second end of the second elongated body 212 has a flexible elongated bar 282 connected to it.

The flexible elongated bar 282 includes the actuating mechanism 218 and locking device 220. The locking mechanism has an engaging section 243 for mating with a receiver 242 located in the connector 232 (described later). The actuating mechanism 218 is used to move the flexible elongated bar 282 to engage and disengage the locking device 220 from the receiver 242.

Disposed in the second elongated body is the clamping device 226 having a clamping end 228 and a connecting end 230. The clamping end 228 of the clamping device has a first jaw member 234 and a second jaw member 236 opposing the first jaw member. First arm 235 and second arm 237 join the connecting end 230 to the first jaw member and second jaw member. The connecting end 230 of the clamping device 226 is affixed to the inside of the first elongated body 202 with the connector 232 which is disposed in the first end 204 of the elongated body 202.

Figure 8B:
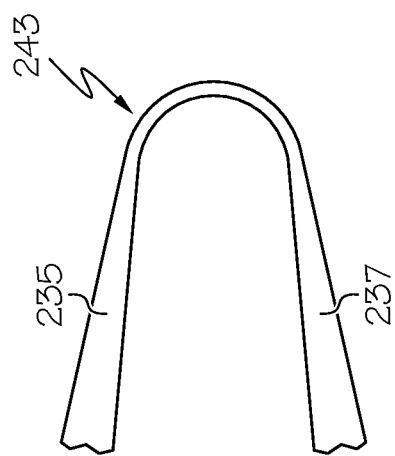
FIG. 8B is a section view of another connecting end of a clamping device of the invention.
Figure 8A:
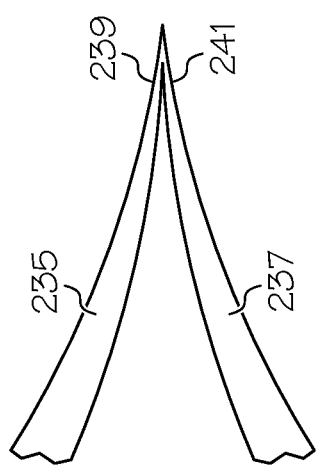
FIG. 8A is a section view of a connecting end of a clamping device of the invention.

Typically, the first jaw member 234 and the second jaw member 236 are biased away from each other when they are in the relaxed position, as shown in FIG. 6. Various methods can be used to bias the first and second jaw member away from each other. For example, the material used to make the clamping device may be a spring steel that will allow the first and second jaw members to flex inward and outward. End 239 of the first arm 235 and end 241 of the second arm 237 may be fused together as shown in FIG. 8A to cause the first jaw member 234 and the second jaw member 236 to bias away from each other. Also, clamping device 226 may be made from a single piece of material with the connecting end 230 bent to create a spring 243 as shown in FIG. 8B. Alternatively, a spring 238 may be disposed between the first arm 235 and the second arm 237 as shown in FIG. 6.

The connector 232 is sized to fit inside the substantially hollow portion 208 of the first elongated body 202 and is spaced a distance 276 from an interior surface 209 of the first elongated body to allow the bar 280 to pass between the connector 232 and the interior surface 209. The connector 232 defines a hollow interior portion 231 sized to receive the engaging section 243 of the flexible elongated bar 282. Disposed in the hollow interior portion 231 is a receiver 242 that mates with the engaging section 243 of the locking device 220. In this embodiment, the receiver 242 is a tooth and the engaging section 243 is a serrated edge that mates with the tooth. Other locking mechanisms may also be used. For example, the receiver could be a serrated edge that mates with a tooth of the engaging section.

Similar to the embodiment described previously, the first jaw member 234 may have a pin 258 that aligns with a hole 260 with a diameter sized to receive the pin located in the second jaw member 236 to align the jaws in the lateral direction. Alternatively, the second jaw member 236 may have the pin and the first jaw member 234 may have the hole for receiving the pin.

The jaws may also have a relief for receiving a tool such as a needle. As shown in FIG. 6, the first jaw 234 has a relief 264 and the second jaw 236 has a relief 266. Typically, the reliefs are sized to fit the intended tool, such as a needle and are cut in a shape to match the tool. For example, if the jaws were made to hold a round needle, the relief 264 would be a semicircle and the relief 266 would be a semicircle. Alternatively, only one jaw may have a relief for grasping a tool and the other jaw may not have a relief.

Figure 7A:
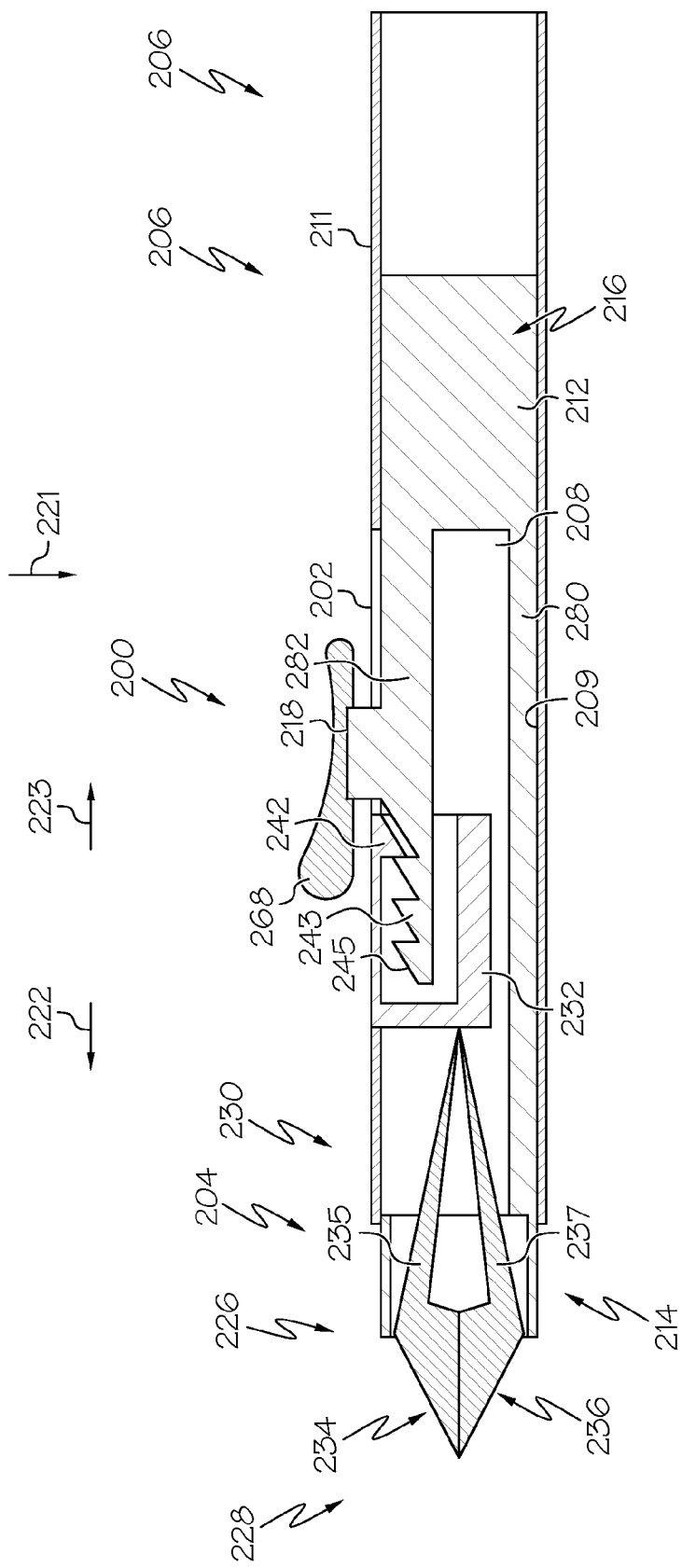
FIG. 7A is another section view of the needle driver of FIG. 6 with the jaws in the closed position.
Figure 7B:
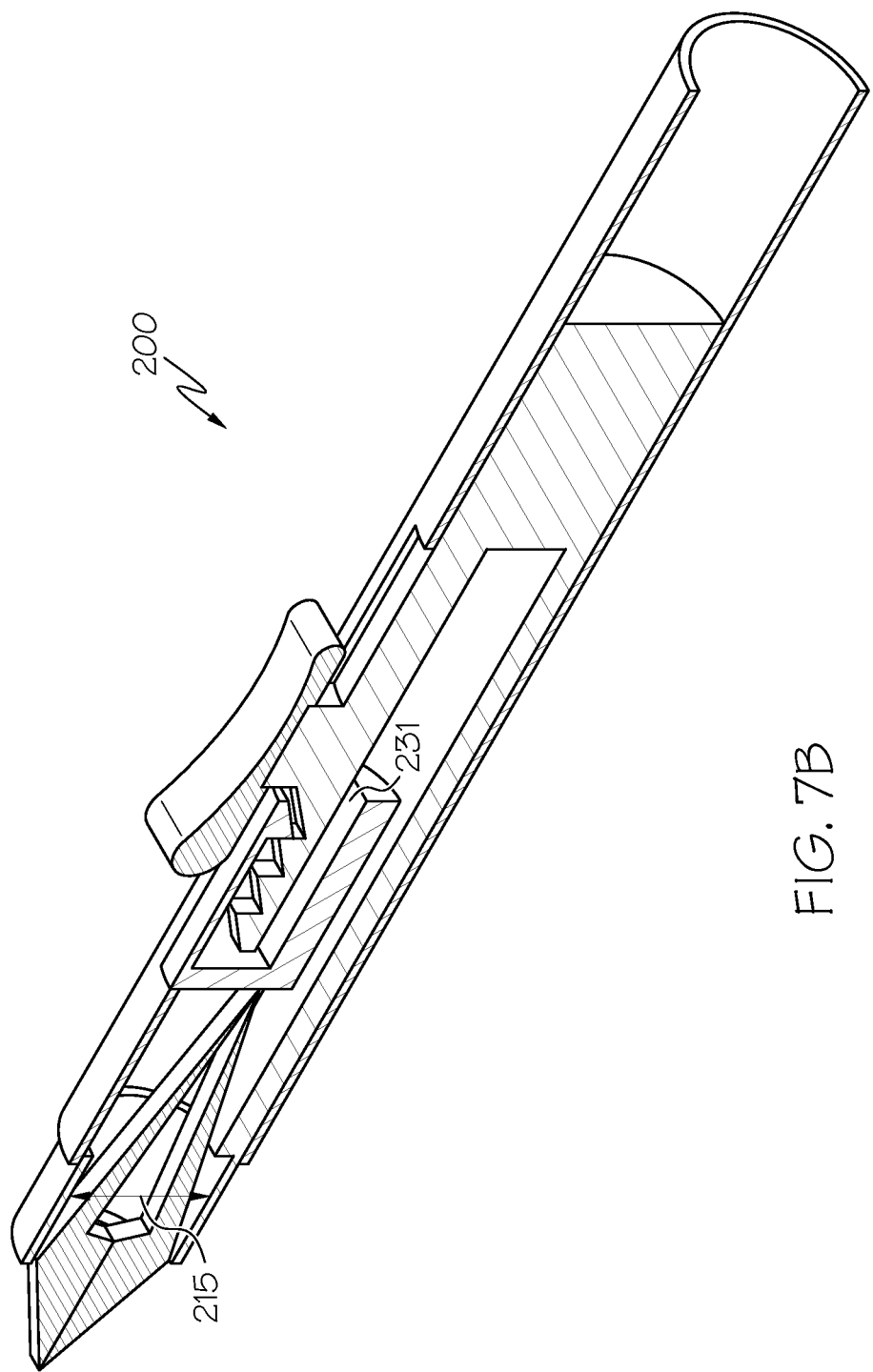
FIG. 7B is a perspective view of the needle driver of FIG. 6.

In operation, a user holds the first elongated body in a hand with a digit on a digit receiver 268. If the opposing jaws are closed, as shown in FIG. 7A, the user pushes the digit receiver in the direction of arrow 221 to disengage the engaging section 243 from the receiver 242 and then slides the digit receiver in the direction of arrow 223, thereby sliding the second elongated body 212 in the direction of arrow 223. The tension in the arms, or the spring 238, which bias the first jaw member and second jaw member away from each other, cause the first and second jaw members to separate creating a gap 270 between them. The user then inserts a tool, such as a needle for suturing, between the first jaw member and the second jaw member and moves the actuator 218 in the direction of arrow 222 to clamp the tool between the first and second jaws.

As the actuator 218 is moved in the direction of arrow 222, a tooth 245 of the engaging section 243 on the flexible elongated bar 282 engages with the receiver 242 located on the interior portion 231 of the connector 232. The actuator can be locked in a predetermined number of positions depending on where the receiver 242 aligns with the teeth of the engaging section 243 of the flexible elongated bar 282. In this manner, the user can adjust the clamping force on the tool and can grasp, secure, and lock tools of a varying size between the first and second jaws. Grasping and releasing a tool and suturing are completed as described in the earlier embodiment.

Figure 9A:
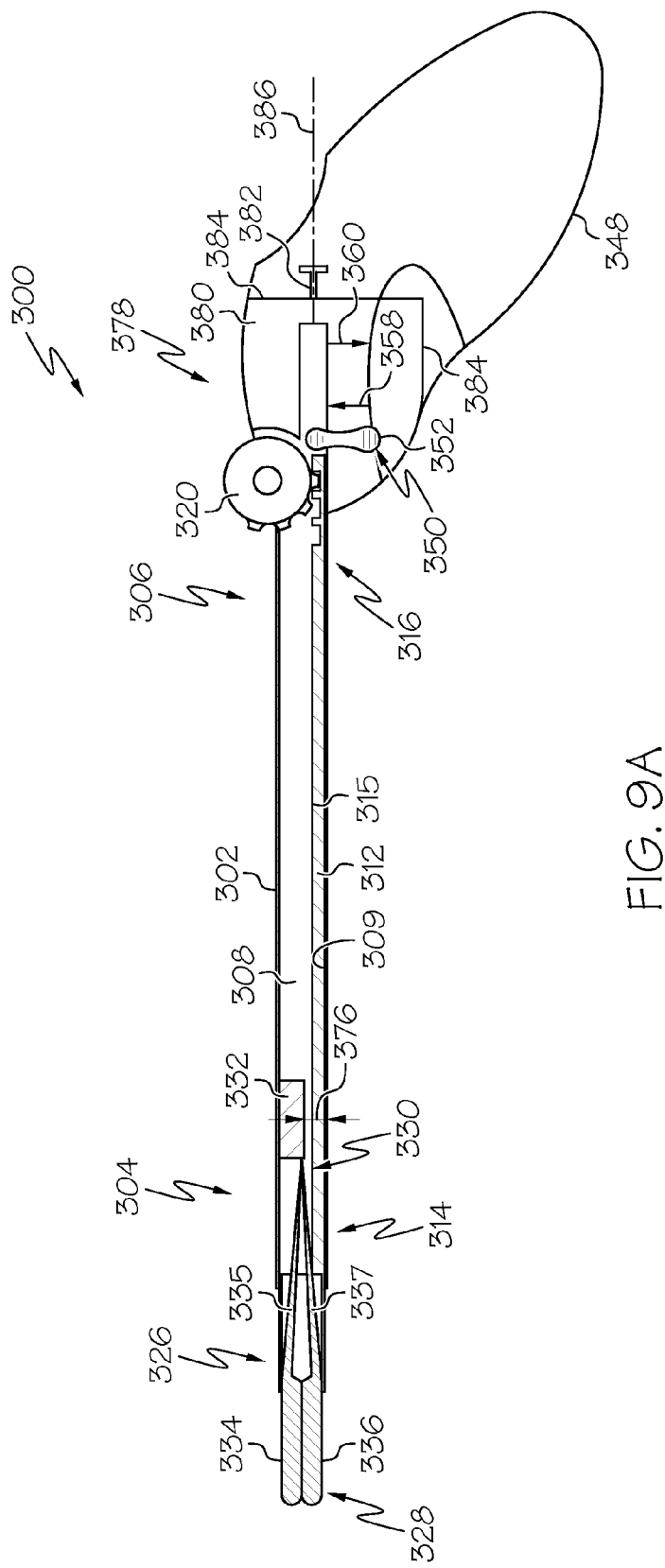
FIG. 9A is a section view of another embodiment of a needle driver of the invention.
Figure 9B:
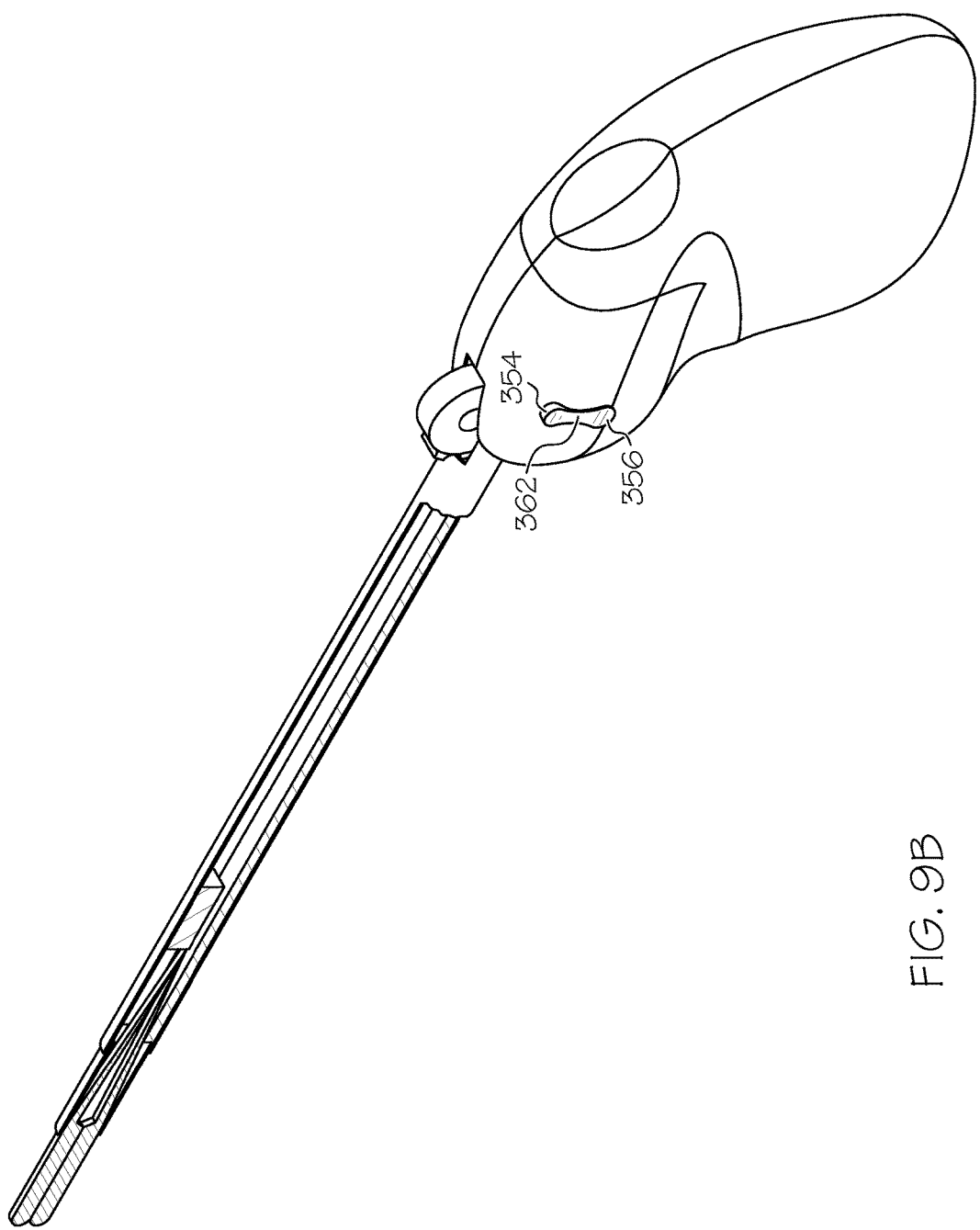
FIG. 9B is a perspective view of the needle driver of FIG. 9A.

Another embodiment is shown in FIGS. 9A and 9B. The needle driver 300 could be used in traditional surgery or in laproscopic surgery. The needle driver 300 has a first elongated body 302 having a first end 304, a second end 306, and a substantially hollow interior portion 308. At least a portion of the first elongated body has a substantially hollow portion 308. Slideably disposed in first elongated body 302 is a second elongated body 312 having a substantially hollow first end 314 and a second end 316. A connector 332 is sized to fit inside the substantially hollow portion 308 of the first elongated body 302 and is spaced a distance 376 from an interior surface 309 of the first elongated body to allow shaft 315 to pass between the connector 332 and the interior surface 309.

Figure 10:
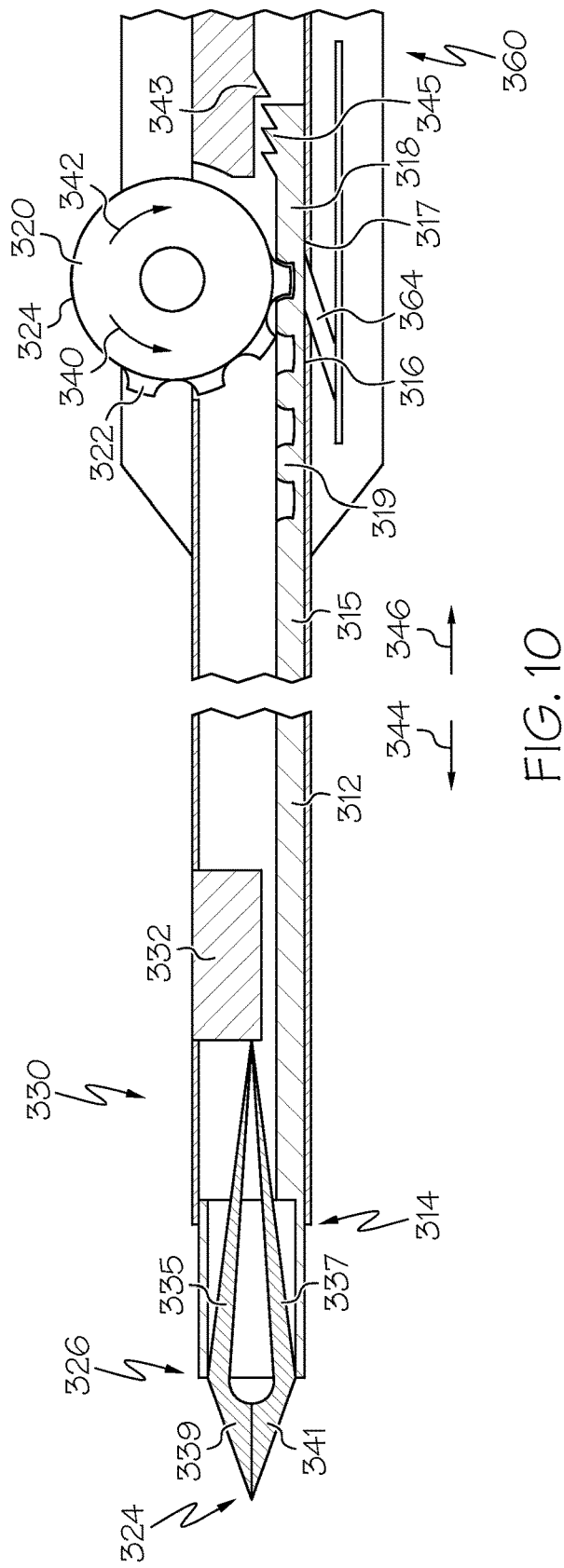
FIG. 10 is a section view of another embodiment of the needle driver of the invention.

As shown in FIGS. 9A, 9B, and 10, disposed in the first elongated body 302 is a clamping device 326 having a clamping end 328 and a connecting end 330. The connecting end 330 of the clamping device 326 is affixed to the inside of the first elongated body 302 with a connector 332. The clamping end 328 of the clamping device has a first jaw member 334 and a second jaw member 336 opposing the first jaw member. First arm 335 and second arm 337 connect the connected end 314 to the first jaw member and second jaw member. The jaws may be made to spring apart by any of the methods described previously, may have the pin and hole alignment mechanism described previously, and may have the reliefs for holding a tool as described previously. The jaws 334 and 336 shown in FIG. 9A are blunted to avoid tissue damage. The jaws 334 and 336 are typically used for holding and moving tissue instead of operating tools, such as needles. Alternatively, the jaws could be first jaw 339 and second jaw 341 designed to hold tools similar to the jaws 134 and 136 of FIG. 2A. Additionally, the blunt jaws 334 and 336 could be used instead of the tool holders on the other embodiments shown herein.

A handle 348 may be disposed on the second end 306 of the first elongated body 302. The handle allows the user to grasp and maneuver the needle driver by palming the driver. Disposed on the side of the handle is a lock 350 that is used to lock the shaft 315 in a certain position, thereby locking the jaws in a certain position. For example, the lock may be used to lock the jaws in an open position, in a closed or clamping position, or in an intermediate position. The lock may be a slide, a pivoting push button lock, or other type of lock. As a slide lock, the user slides a lock button 352 upward in the direction of arrow 358, which causes the lock to engage with the shaft 315 and prevent the shaft from moving until the lock button is slid downward in the direction of arrow 360, thereby unlocking the shaft. In an alternative design, the button may be slid downward in the direction of arrow 360 to lock the shaft and upward in the direction of arrow 358 to unlock the shaft. In a design shown in FIG. 9B, the lock button 352 pivots about its center 362. To lock the shaft 315, the user pushes the upper portion 354 of the lock button 350 inward towards the handle 348, causing the upper portion of the lock button to move inwardly towards the handle and a lower portion 356 of the lock button to move outwardly away from the handle. To unlock the shaft 315, the user pushes the lower portion 356 of the lock button 352 inwardly toward the handle.

The first end 314 of the second elongated body 312 is constructed similar to those described previously to slide over the first and second jaw members to open and close the first and second jaw members. The first end 314 and the second end 316 are connected by a shaft 315. The second end 316 of the driver includes a rack 318 with a first set of teeth 319 that mates with a second set of teeth 322 disposed on a perimeter 324 of a rotatable actuator 320. A spring 364 biases against an underside 317 of the rack 318 to hold the rack against the rotatable actuator 320. When the operator pushes the rotatable actuator 320 down, it compresses spring 364 and unlocks a tooth 343 from teeth 345. When the actuator is rotated in the direction of arrow 340, typically with one of the user's digits such as a finger or thumb, the shaft 315 moves in the direction of arrow 346, thereby sliding the second end 316 of the driver in the direction of arrow 346 and allowing the jaws 334 and 336 to open. When the actuator is rotated in the direction of arrow 342, the shaft 315 moves in the direction of arrow 344, thereby sliding the second end of the driver in the direction of arrow 344 and closing the jaws 334 and 336. While not shown in FIG. 10, a handle such as handle 348 of FIG. 9A, is typically included in the second end 360. Alternatively, a handle with a bulbous end such as that shown in FIG. 13 may be disposed on the second end 360.

Referring back to FIG. 9A, another embodiment has an operating portion 378 comprising the lock 350, the actuator 320, the first elongated body 302, the clamping device 326, and a body 380 may be connected to the handle 348 and rotate on a pin 382. A parting line 384 shows the separation between the operating portion 378 and the handle 348. The operating portion 378 pivots about a center axis 386 of the pin 382. In this embodiment, a user can hold the handle 348 in a palm and rotate the operating portion 378 with digits to thereby rotate the clamping device 326 relative to the first elongated body without having to rotate the entire needle driver 300.

FIG. 12A shows another embodiment of a needle driver 400 of the invention. The needle driver has an elongated body 402 having a first end 404 and a second end 406. At least a portion of the first elongated body has a substantially hollow portion 408 defined by an interior dimension 410. An outer surface 403 of the first elongated body may be knurled to allow the user to maintain a positive grip on the needle driver. Slideably disposed in the elongated body 402 is an actuator 418 affixed to a clamping device 426. The actuator passes through a slot 424 in the elongated body 402, which allows the actuator to slide forward and backward in the direction of arrows 420 and 422 respectively.

The clamping device 426 has a clamping end 428 and a guiding end 430. The guiding end 430 of the clamping device 426 slides in a guide 429 disposed in the elongated body 402. The guide 429 defines a hole 432 with an inside diameter 433 that is larger than an outside diameter 431 of the guiding end 430 of the clamping device 426. The clamping end 428 of the clamping device has a first jaw member 434 and a second jaw member 436 opposing the first jaw member 434. First arm 435 and second arm 437 connect the guiding end to the first jaw member and second jaw member.

Typically, the first jaw member and the second jaw member are biased away from each other when they are in the relaxed position. Various methods can be used to bias the first and second jaw member away from each other. For example, the material used to make the clamping device may be a spring steel that will allow the first and second jaws to flex inward and outward. Alternatively, a spring 438 may be disposed between the first arm 435 and the second arm 437.

As shown in FIG. 12B, the internal dimension 474 of the first end 414 of the elongated body 402 is approximately the same as an external dimension 472 of the first and second jaw members when the members are in a closed position. As such, when the actuator 418 moves to a most rearward position being pushed in the direction of arrow 422 it drives the first jaw member and the second jaw member towards each other, causing the jaw members to clamp together. When the actuator 418 is moved forward in the direction of arrow 420, the first and second jaw members spring away from each other and the jaws open.

A serrated edge 440 having teeth 442 is disposed on an interior portion 441 of the first end 404 of the elongated by body 402. Affixed to the actuator 418 is a locking device 444 with a tooth 446 on a distal end 452 of the flexible bar 448 that mates with the teeth 442. As shown in FIG. 4, a proximal end 454 of the flexible bar 448 is affixed to the actuator 418. Alternatively, there may be a single tooth disposed on the interior portion 441 of the first elongated body and multiple teeth disposed on the distal end 452 of the flexible bar 448. As with the embodiment shown in FIG. 2A, the jaws of the embodiment of FIG. 12A may have reliefs or knurled gripping surfaces or both, and one jaw may have a pin that aligns with a hole in the other jaw to prevent lateral movement.

Figure 13:
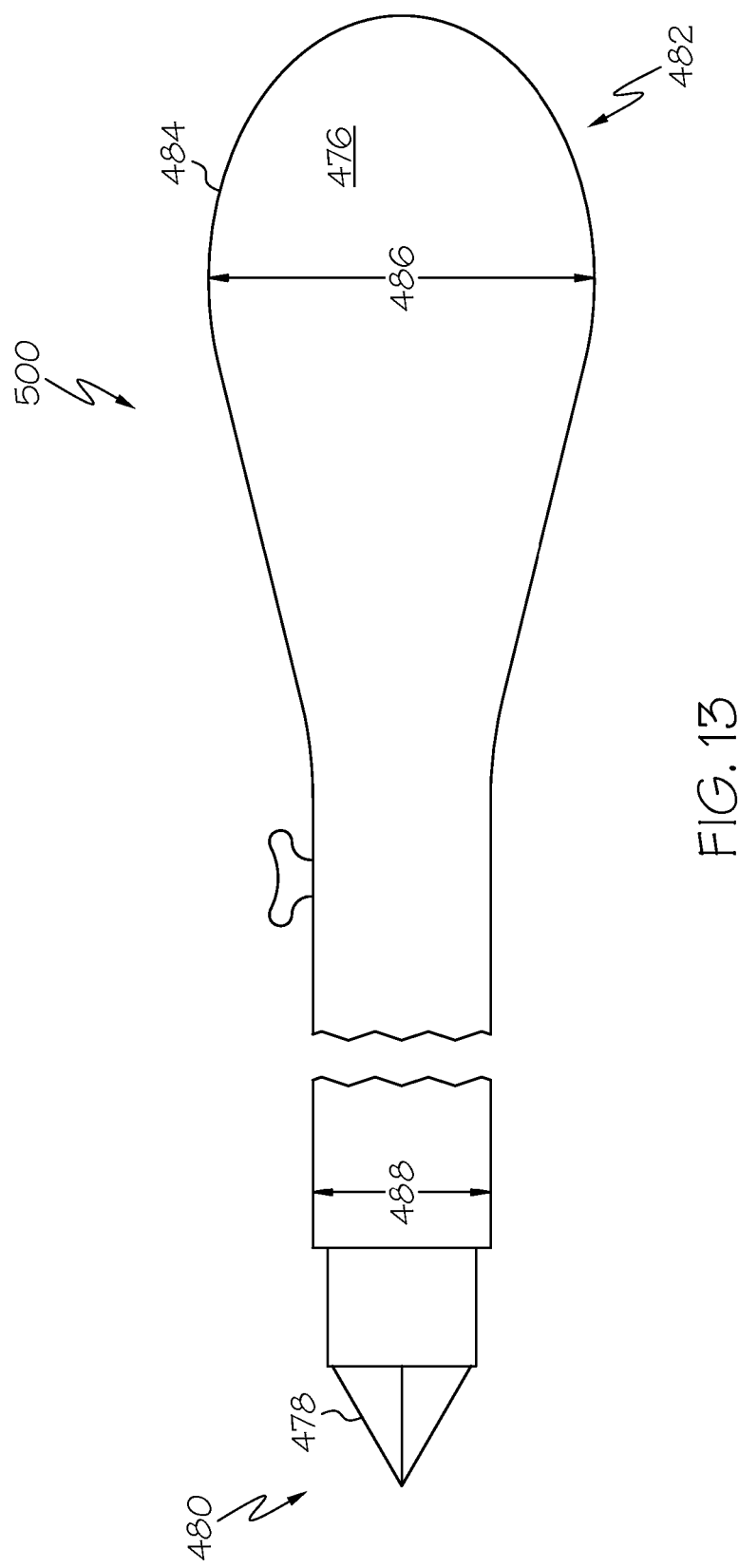
FIG. 13 is a side view of another embodiment of a needle driver having a bulbous second end.

FIG. 13 shows a needle driver 500 with jaws 478 on a first end and a bulbous end 476 disposed on a second end 482 of the needle driver. The bulbous end 476 has a rounded portion 484 that has an outside diameter 486 that is larger than an outside diameter 488 of the first end 480. The bulbous end is sized to fit the hand of a user to allow the user to palm the needle driver instead of holding it between the user's fingers. The bulbous end could also be included as a feature on other embodiments of a needle driver described herein.

FIG. 14 shows an embodiment similar to that of FIG. 10, with the rotatable actuator 320 of FIG. 10 replaced with a slideable actuator 366 affixed to a second end 370 of a shaft 368. A first end 381 of a flexible bar 391 is connected to the slideable actuator 366, and a second end 383 has teeth 392. A user pushes the actuator 366, which has a digit receiver 372, in the direction of arrow 388 to close the jaws. To open the jaws, the user pushes the digit receiver down to release a tooth 394 from the teeth 392 and slides the digit receiver in the direction 390. A spring 387 biases against an underside 389 of a flexible bar 391 to maintain engagement of the teeth 392 with the tooth 394. When the operator pushes the slideable actuator 366 down, it compresses spring 387 and unlocks teeth 392 from tooth 394. While not shown in FIG. 14, a handle, such as handle 348 of FIG. 9A, is typically included on a second end 347. Alternatively, a handle with a bulbous end such as that shown in FIG. 13 may be disposed on the second end 347.

Figure 15:
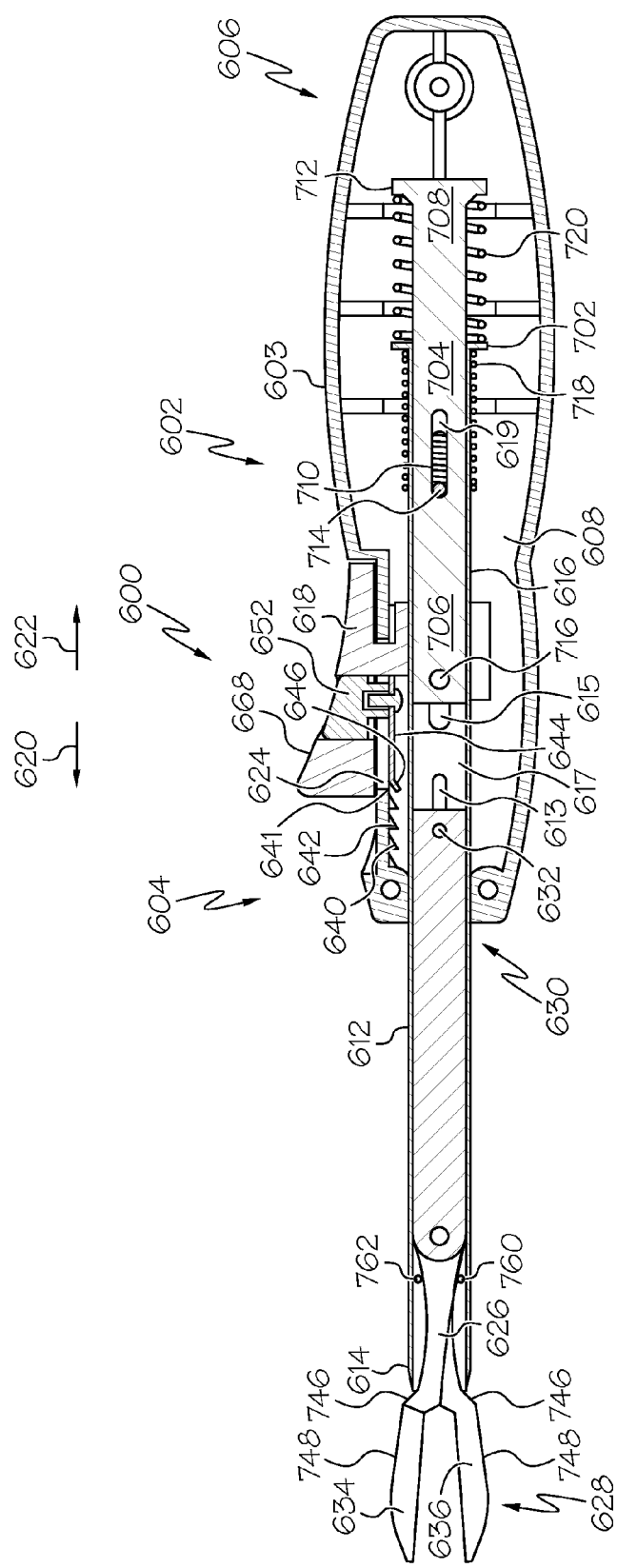
FIG. 15 is a cross-sectional view of a needle driver according to another embodiment.

FIG. 15 shows another embodiment of a needle driver 600 of the invention. The needle driver has a first elongated body 602 having a first, or distal, end 604 and a second, or proximal, end 606. The first elongated body can define an interior chamber 608. An outer surface 603 of the first elongated body may be knurled to allow the user to maintain a positive grip on the needle driver. Slideably disposed in the first elongated body 602 is a second elongated body 612 having a first, or distal, end 614, a second, or proximal, end 616, and a substantially hollow interior portion, or interior space, 617. The second elongated body 612 has a first, or distal, slot 613, a second, or intermediate, slot 615, and a third, or proximal, slot 619. The proximal end 616 of the second elongated body 612 has a proximal flange 702. The first elongated body 602 can include a cradle (not shown) within the interior chamber 608, which can be used to support the second elongated body as it slides within the interior chamber 608. Other structures, which can include connector and pin attachment structures (not shown) can also be disposed within the interior chamber 608.

At least partially disposed in the second elongated body is a clamping device 626 having a clamping end 628 and a connecting end 630. The connecting end 630 of the clamping device 626 is affixed to the inside of the first elongated body 602 with a connector 632. The clamping end 628 of the clamping device has a first jaw member 634 and a second jaw member 636 opposing the first jaw member 634. Each of the first jaw member 634 and the second jaw member 636 can include a relatively steeper ramp 746 and a relatively shallower ramp 748.

Also at least partially disposed in the second elongated body is a biasing shaft 704 having a first end 706, a second end 708, and a slot 710. Affixed to the second end 708 is a proximal flange 712. An actuator 618 is affixed to the biasing shaft 704 with a guide pin 716. The guide pin 716 passes through the intermediate slot 615 in the second elongated body 612. An alignment pin 714 is affixed to the first elongated body 602 and passes through the proximal slot 619 in the second elongated body 612 and through the slot 710 in the biasing shaft 704. A first, or distal, biasing member or spring, 718 is compressed between the pin 714 and the flange 702. A second, or proximal, biasing member or spring, 720 is disposed between the flange 712 and the flange 702. Each of the distal biasing member 618 and the proximal biasing member 620 can be a compression coil spring, as shown in FIG. 15. In other embodiments, the biasing members 618 and 620 can have different configurations. For example, extension springs and/or constant force springs can be used instead of compression coil springs.

The actuator 618 passes through a slot 624 in the first elongated body 602, which allows the actuator 618 to slide forward and backward in the directions of arrows 620 and 622 respectively. A digit receiver 668 designed for receiving a thumb, index finger, or other digit of the user may be affixed to the actuator 618.

A serrated edge 640 having a first plurality of ratchet teeth 642 is disposed on an interior portion 641 of the distal end 604 of the first elongated body 602. The first elongated body 602 can also include a second plurality of ratchet teeth (not shown), which can be laterally spaced from the first plurality of ratchet teeth 642. The first plurality of ratchet teeth 642 and the second plurality of ratchet teeth can extend inwardly from the distal end 604 of the first elongated body into the interior chamber 608. Affixed to the actuator 618 is a locking device 644 with a tooth 646 that mates with the teeth 642 disposed on the distal end 604 of the first elongated body 602. The locking device 644 is connected to a button, or lock release member, 652, used to engage and disengage the tooth 646 from the teeth 642.

When the second elongated body 612 is in a most proximal position as shown in FIG. 15, the first jaw member 634 and the second jaw member 636 are open. The distal spring 718 holds the second elongated body 612 in the most proximal position. When the actuator 618 is moved forward in the direction of arrow 620, it slides the biasing shaft 704 in the direction of arrow 620. The proximal spring 720 pushes the second elongated shaft 612 in the direction of arrow 620, which causes the second elongated shaft 612 to slide over the first jaw member 634 and second jaw member 636, thereby closing the jaw members.

With the tooth 646 locked in the teeth 642, the actuator is locked in a forward position, thereby holding the biasing shaft 704 in a forward position. With the biasing shaft 704 in a forward position, the proximal spring 720 holds the second elongated shaft, or body, 612 in the forward position. Because the proximal spring 720 is compressible and the slot 615 that allows the pin 716 to slide in the second elongated shaft 612, the second elongated shaft, or body, 612 may move less than the biasing shaft 704 when the biasing shaft 704 is moved in the direction of arrow 620. One factor that affects how far the second elongated shaft, or body, 612 travels is the size of the object that is being grasped between the first jaw member 634 and the second jaw member 636.

To retract the second elongated shaft 612 in the direction of arrow 622, the user pushes button 652 to disengage the tooth 646 from teeth 642 and slides the actuator 618 in the direction of arrow 622. The needle driver 600 can include a first cam member 760 and a second cam member 762, which can be secured to the second elongated body 612 and can extend into the interior space 617. The first cam member 760 can bias, or force, the first jaw member 634 to the open position shown in FIG. 15, and the second cam member 762 can bias, or force, the second jaw member 636 to the open position shown in FIG. 15, as the second elongated body 612 is retracted.

Figure 16:
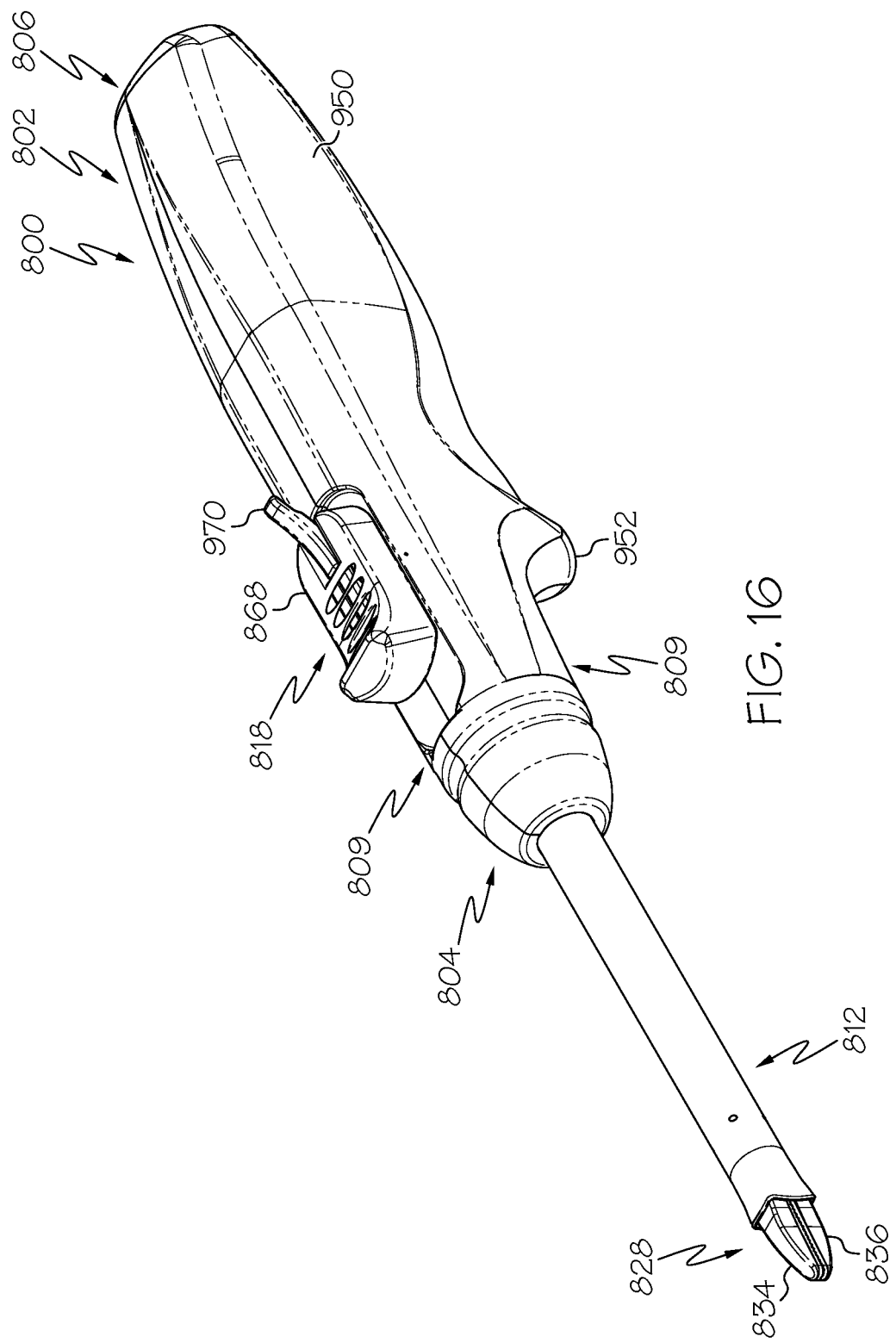
FIG. 16 is a perspective view of a needle driver according to yet another embodiment.
Figure 17:
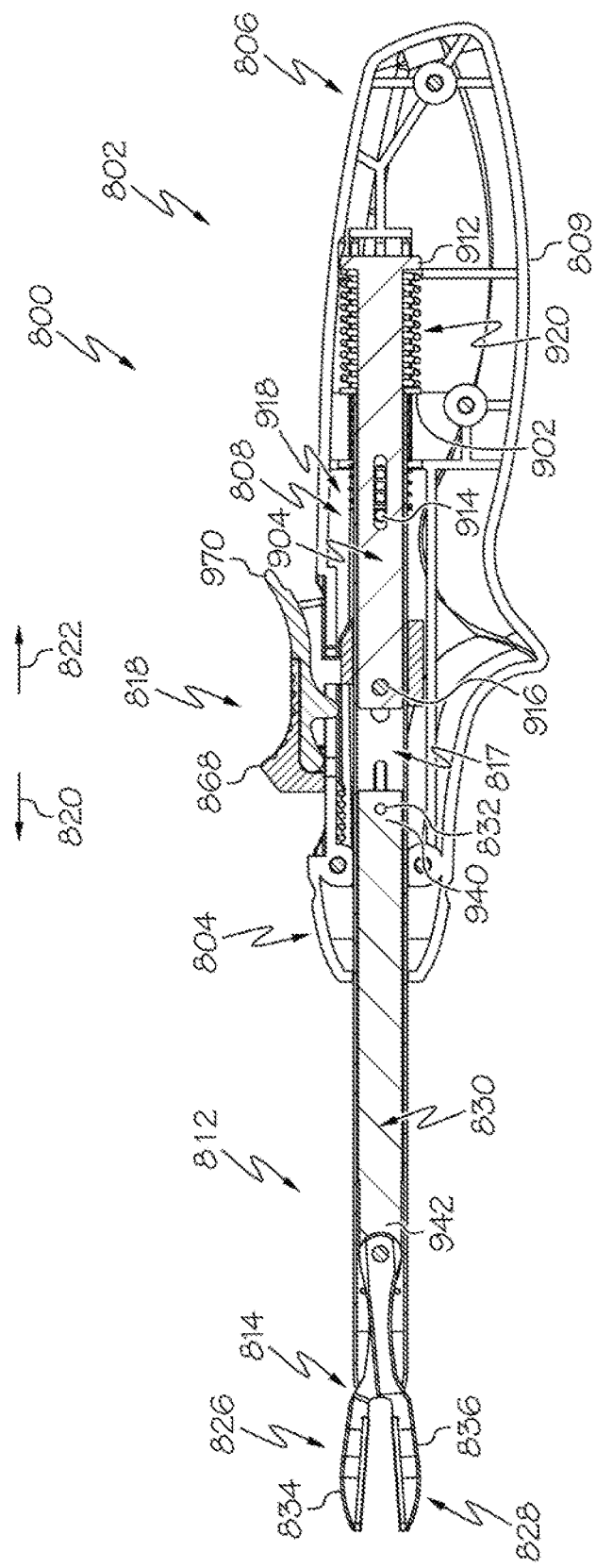
FIG. 17 is a cross-sectional view, shown partially in elevation, of the needle driver of FIG. 16, with a clamping end of a clamping device of the needle driver being depicted in an open position.
Figure 18:
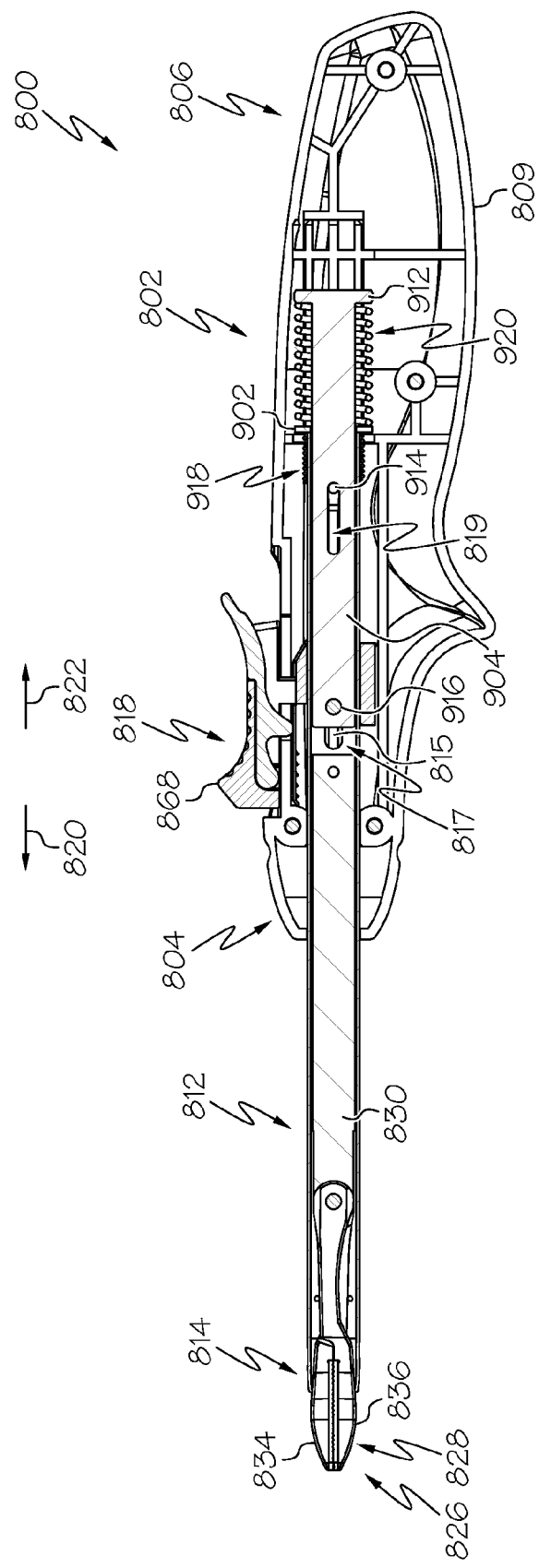
FIG. 18 is a cross-sectional view similar to FIG. 17, but with the clamping end of the clamping device being depicted in a closed position.
Figure 19:
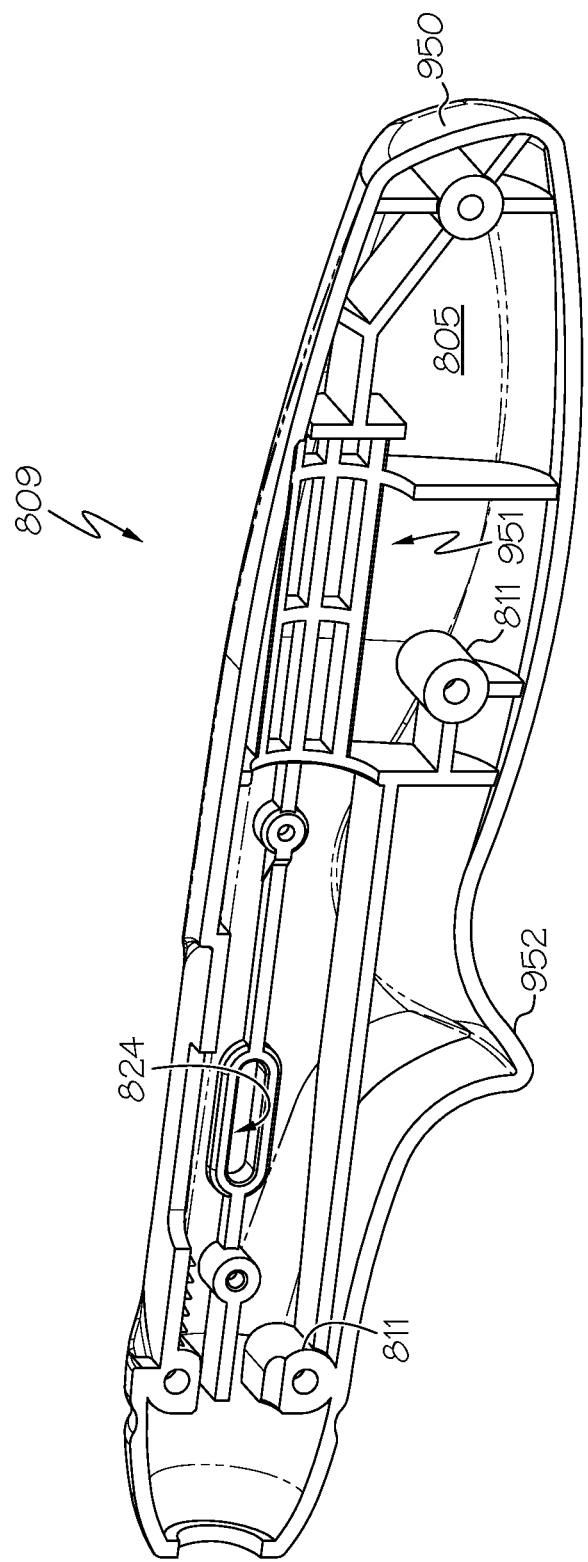
FIG. 19 is a perspective view of one portion of a first elongated body of FIG. 16.
Figure 22:
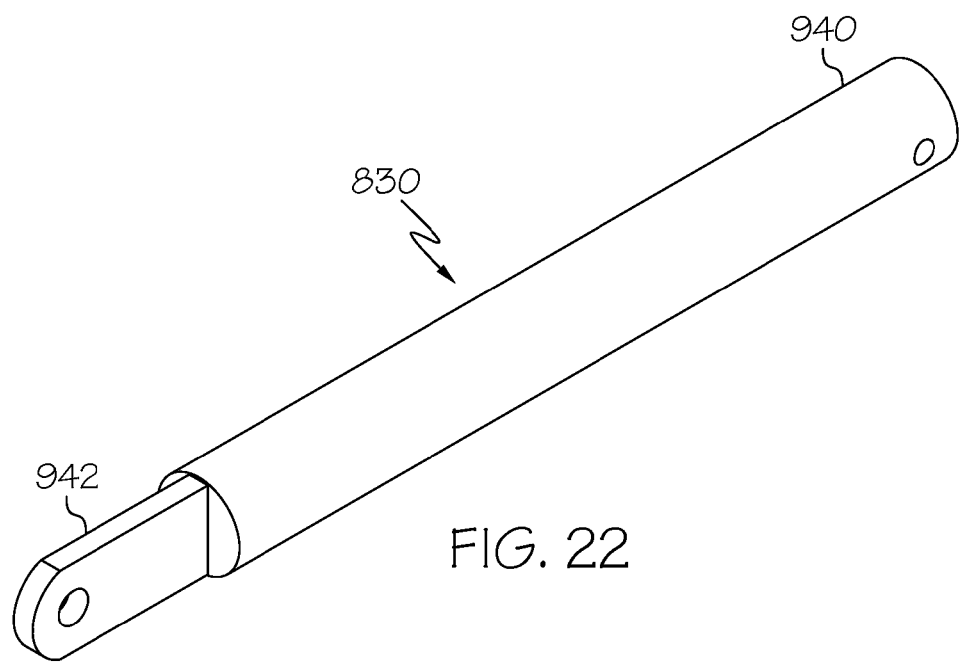
FIG. 22 is a perspective view of a connecting member of the clamping device of the needle driver of FIG. 16.

FIGS. 16-18 illustrate a needle driver 800, according to another embodiment. The needle driver 800 can include a first elongated body 802, which can include a distal end 804 and a proximal end 806. The first elongated body 802 can define an interior chamber 808. The first elongated body can include two portions 809, with one of the portions 809 being illustrated in FIG. 19. The two portions 809 can cooperate to define the interior chamber 808, and can be attached to each other in any suitable fashion. In one embodiment, the two portions 809 can be fastened to each other. Referring to FIG. 19, one of the portions 809 can include a plurality of bosses 811, which can extend inwardly from an interior surface 805 of the first elongated body 802. The bosses 811 can be configured to receive fasteners, such as screws, extending through the other portion 809 of the first elongated body 802. The first elongated body 802 can also include a cradle 951 (shown partially in FIG. 19) disposed within the interior chamber 808. The first elongated body 802 can have an ergonomic shape, as shown in FIG. 16, which can assist a healthcare professional, for example, a physician, with grasping the needle driver 800.

The needle driver 800 can include a second elongated body 812, which can include a distal end 814 and a proximal end 816 (FIG. 20). The second elongated body 812 can define an interior space 817, and can be slideable, or movable, within the interior chamber 808 defined by the first elongated body 802, between a retracted position shown in FIG. 17 and an extended position shown in FIG. 18. The second elongated body 812 can slide in a proximal direction 822 toward the retracted position and in a distal direction 820 toward the extended position. The cradle 951 of the first elongated body 802 can support the second elongated body 812 as it slides within the interior chamber 808. The second elongated body 812 can define a distal slot 813, an intermediate slot 815, and a proximal slot 819. The proximal end 816 of the second elongated body 812 can include a proximal flange 902. The needle driver 800 can include a clamping device 826, which can include a clamping end 828 and a connecting member 830. A proximal end 940 of the connecting member 830 can be affixed to the first elongated body 802, for example with a connector 832 (FIG. 17). The connector 832 can extend through the distal slot 813 defined by the second elongated body 812, and can be affixed, or secured, to each of the first elongated body 802 and the connecting member 830. The connecting member 830 can be disposed within the second elongated body 812, as shown in FIGS. 17 and 18.

The clamping end 828 of the clamping device 826 can include a first jaw member 834 and a second jaw member 836 opposing the first jaw member 834. Each one of the first jaw member 834 and the second jaw member 836 can be pivotally coupled with a distal end 942 of the connecting member 830. As shown in FIGS. 23 and 24, the clamping device 826 can include a first arm 835 and a second arm 837. The first arm 835 can pivotally couple the first jaw member 834 with the connecting member 830, and the second arm 837 can pivotally couple the second jaw member 836 with the connecting member 830. Each one of the first jaw member 834 and the second jaw member 836 can be pivotable, about a pivot member 944 (FIGS. 23 and 24), between an open position shown in FIGS. 17 and 24 and a closed position shown in FIGS. 18 and 23. Referring to FIGS. 23 and 24, each of the first jaw member 834 and the second jaw member 836 can include a relatively steeper ramp 946 and a relatively shallower ramp 948.

A biasing shaft 904 can be slidable relative to each of the first elongated body 802 and the second elongated body 812, and can be partially disposed within the interior chamber 808 defined by the first elongated body 802, and partially disposed within the interior space 817 defined by the second elongated body 812, as shown in FIGS. 17 and 18. The biasing shaft 904 can include a proximal flange 912, and can define a slot 910 (FIG. 21). The slot 910 can be sized and configured to receive an alignment pin 914 (FIGS. 17 and 18). The alignment pin 914 can be affixed to the first elongated body 802, and can extend through the proximal slot 819 (FIG. 20) defined by the second elongated body 812, and through the slot 910 (FIG. 21) defined by the biasing shaft 904. The alignment pin 914 can slide within the proximal slot 819 and the slot 910, which can permit each of the second elongated body 812 and the biasing shaft 904 to slide relative to the first elongated body 802, and can permit the biasing shaft 904 to slide relative to the second elongated body 812.

Needle driver 800 can include a distal biasing member 918 and a proximal biasing member 920. Each of the distal biasing member 918 and the proximal biasing member 920 can be a compression coil spring as shown in FIGS. 17 and 18. In other embodiments, the biasing members 918 and 920 can have different configurations. For example, extension springs and/or constant force springs can be used instead of compression coil springs. The proximal biasing member 920 can be relatively stiffer, and can be substantially stiffer, than the distal biasing member 918. For example, the proximal biasing member 920 can have a spring constant that can be greater, and can be substantially greater, than a spring constant of the distal biasing member 918. The proximal biasing member 920 can extend between the biasing shaft 904 and the second elongated body 812. As shown in FIGS. 17 and 18, the proximal biasing member 920 can extend between the proximal flange 902 of the second elongated body 812 and the proximal flange 912 of the biasing shaft 904. The distal biasing member 918 can be compressed between the alignment pin 914 and the proximal flange 902 of the second elongated body 812.

Needle driver 800 can include an actuator 818 (FIGS. 16-18), which can be affixed to the biasing shaft 904, for example, with a guide pin 916 (FIGS. 17 and 18) secured to each of the actuator 818 and the biasing shaft 904. The guide pin 916 can extend through the intermediate slot 815 defined by the second elongated body 812, which can permit the actuator 818 and the biasing shaft 904 to slide relative to the second elongated body 812. The actuator 818 can extend through a slot 824 (FIG. 19) defined by the first elongated body 802. Actuator 818 can include a digit receiver 868, which can extend above an exterior surface 950 of the first elongated body 802, as shown in FIG. 16. The digit receiver 868 can be shaped to comfortably receive a digit (e.g., a thumb or index finger) of a healthcare professional using the needle driver 800. The exterior surface 950 of the elongated body 802 can be contoured to receive the palm of a hand of a user. As shown in FIG. 16, the elongated body 802 can also include a lower protrusion 952, which can be shaped to receive another digit of the user, for example a middle finger. The combined features of the actuator 818 and the first elongated body 802 can provide an ergonomic design that can facilitate comfortably grasping and manipulating the needle driver 800.

Figure 25:
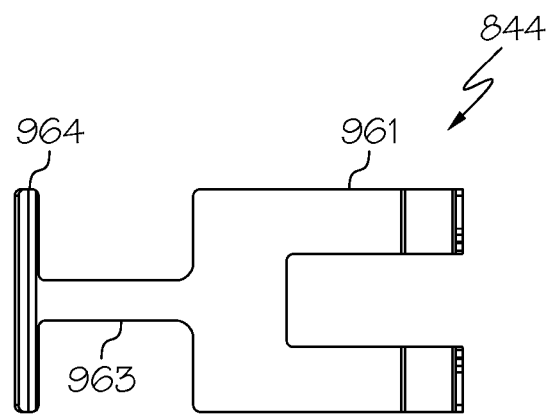
FIG. 25 is a bottom plan view of a locking device of the needle driver of FIG. 16.
Figure 26:
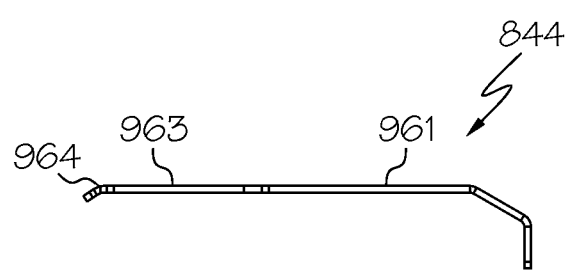
FIG. 26 is a side elevational view of the locking device of FIG. 25.
Figure 28:
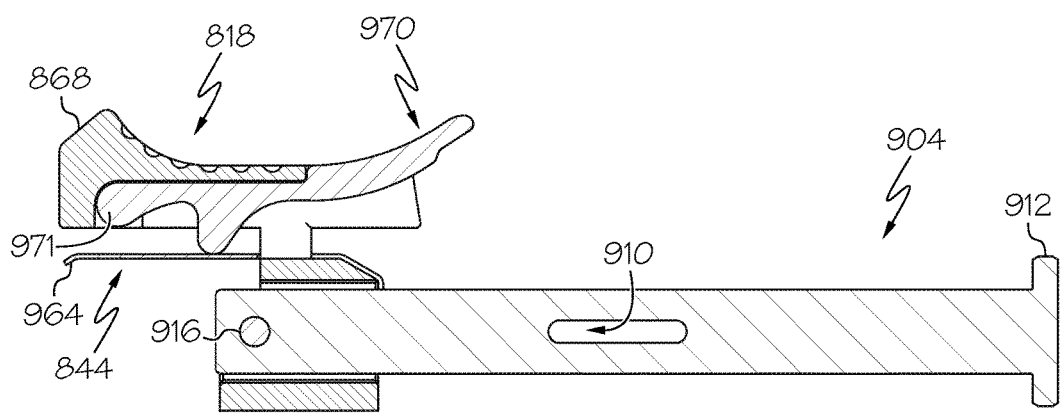
FIG. 28 is a fragmentary cross-sectional view depicting the biasing shaft, an actuator, a lock release member, and the locking device of the needle driver of FIG. 16, with selected portions of the needle driver omitted for purposes of illustration, with the locking device being depicted in a non-deflected configuration, corresponding to a locked configuration of the actuator.
Figure 29:
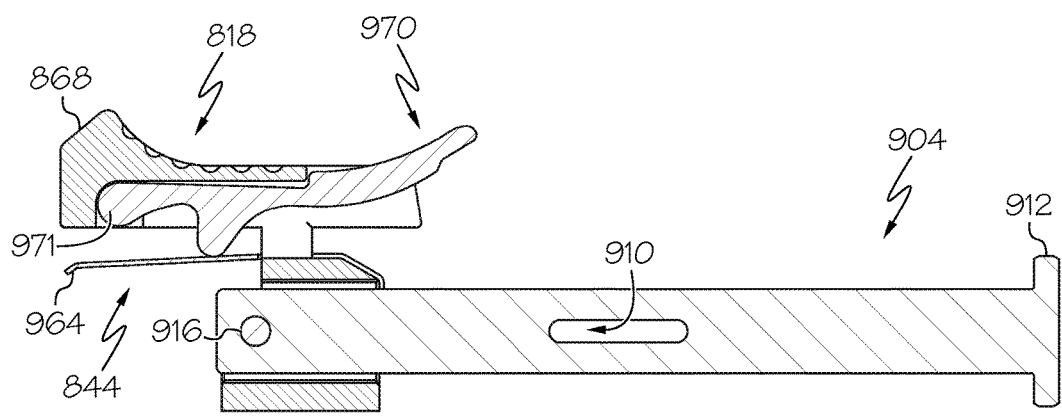
FIG. 29 is a fragmentary cross-sectional view similar to FIG. 28, but with the locking device being depicted in a deflected configuration, corresponding to an unlocked configuration of the actuator.

A locking device 844 (FIGS. 25-26 and 28-29) can be attached to the actuator 818, and can be movable with the actuator 818 proximally and distally. As shown in FIGS. 25-26, the locking device 844 can include a base portion 961, a flexible arm 963 extending distally away from the base portion 961, and a distal tooth 964. Alternatively, the locking device 844 can include more than one tooth, i.e., one or more teeth in addition to the distal tooth 964, with the additional teeth spaced proximally from the distal tooth 964 and from each other. The flexible arm 963 can connect the base portion 961 and the distal tooth 964. The base portion 961, flexible arm 963, and the distal tooth 964 can be formed as a unitary construction. A lock release member 970 (FIGS. 17-18 and 28-29) can be coupled with the actuator 818. As shown in FIGS. 28 and 29, the lock release member 970 can be a lever, which can be pivotally coupled with the actuator 818. A distal end 971 (FIGS. 28 and 29) of the lock release member 970 can include a pair of pin-like bosses which can nest into pockets (not shown) in the actuator 818. The lock release member 970 can be pivotable between a relaxed position shown in FIG. 28 and an actuated position shown in FIG. 29.

As shown in FIG. 27, the first elongated body 802 can include a first plurality of ratchet teeth 976 and a second plurality of ratchet teeth 978, which can extend inwardly from the distal end 804 of the first elongated body 802 into the interior chamber 808 defined by the first elongated body 802. The ratchet teeth 976 can be laterally spaced from the ratchet teeth 978. The distal tooth 964 of the locking device 844 can have a shape that is complementary with the shape of the ratchet teeth 976 and the ratchet teeth 978. In alternate embodiments (not shown), the first elongated body 802 can include only a single plurality of ratchet teeth (e.g., 976 or 978), which can be positioned laterally to the left or right of a centerline axis of the first elongated body 802, or can be positioned to straddle the centerline axis. The distal tooth 964 can be sized to simultaneously engage corresponding ones of the ratchet teeth 976 and the ratchet teeth 978, as the actuator 818 and the locking device 844 slide distally, as the second elongated body 812 moves from the retracted position to the extended position. As the locking device 844 slides distally, the distal tooth 964 can slide along an inclined surface of one of the ratchet teeth 976 and a corresponding one of the ratchet teeth 978, until the distal tooth reaches the apex of each of the corresponding ratchet teeth 976 and 978. Due to the flexibility of the flexible arm 963, further distal movement of the locking device 844 can cause the distal tooth 964 to snap into a gap between adjacent ones of the ratchet teeth 976 and a gap between adjacent ones of the ratchet teeth 978, to releasably lock the actuator. This process can be repeated, with other adjacent pairs of the ratchet teeth 976 and the ratchet teeth 978, as the locking device 844 moves further in the distal direction 820, which permits the actuator 818 to be releasably locked in a predetermined number of positions. This, in turn, permits the second elongated body 812 to be releasably locked in a predetermined number of positions.

In other embodiments (not shown), the needle driver 800 can be configured to provide non-discrete releasable locking of the actuator 818, i.e., not limited to a predetermined number of locking positions. For example, the ratchet teeth 976 and 978 can be eliminated, and the necessary friction force to releasably lock the actuator 818 can be achieved by controlling the surface finish or rigidity of the interior surface 805 of the first elongated body 802, and configuring an arm of a locking device to engage the interior surface 805. The arm of the locking device can include one or more teeth, or no teeth. Locking device arms having varying rigidity can be used. In embodiments using a relatively rigid locking device arm, the arm can be biased, or forced, into engagement with the interior surface 805 by a biasing member (not shown). The biasing member can extend between the locking device arm and an opposing surface within the interior chamber 808 defined by the first elongated body 802, or can extend between the locking device arm and the second elongated body 812, with the biasing member being configured to translate relative to the second elongated body 812 for non-impacted movement of the actuator 818.

In operation, the needle driver 800 can be used to grasp and manipulate a tool, for example a needle such as the needle 284 shown in FIG. 11. The user, for example a healthcare provider such as a physician, can grasp the first elongated body 802, with a first digit placed on the digit receiver 868 of the actuator 818, and a second digit pressed against the protrusion 952 of the first elongated body 802. The ergonomic shape of the first elongated body 802 can comfortably accommodate the palm of the user's hand. The user can slide the actuator 818 in the proximal direction 822 to place the second elongated body 812 in the retracted position shown in FIG. 17. In this position, the first jaw member 834 and the second jaw member 836 are in the respective open position, shown in FIG. 17, such that there is a gap between the first jaw member 834 and the second jaw member 836. The first jaw member 834 can be biased, or forced, to the open position by a first cam member 960, which can be secured to the second elongated body 812 and can extend inwardly into the interior space 817 defined by the second elongated body 812. As shown in FIGS. 23 and 24, the first cam member 960 can be positioned below the first arm 835 and can slide along a lower surface of the first arm 835, forcing the first arm 835 and the first jaw member 834 to pivot to the open position shown in FIG. 24. Similarly, the second jaw member 836 can be biased, or forced, to the open position by a second cam member 962, which can be secured to the second elongated body 812 and can extend into the interior space 817. As shown in FIGS. 23 and 24, the second cam member 962 can be positioned above the second arm 837, and can slide along an upper surface of the second arm 837, forcing the second arm 837 and the second jaw member 836 to pivot to the open position shown in FIG. 24.

With the first jaw member 834 and the second jaw member 835 in the open position, the user can insert a tool, for example a needle used for suturing, between the first jaw member 834 and the second jaw member 836, and can then slide the actuator 818 in the distal direction 820. As the actuator 818 slides distally, the biasing shaft 904 also slides distally. This causes the relatively stiffer proximal biasing member 920 to push the second elongated body 812 in the distal direction 820. As the second elongated body 812 slides distally relative to the first elongated body 802, the distal end 814 of the second elongated body 812 can contact the first jaw member 834 and the second jaw member 836. The distal end 814 of the second elongated body 812 can initially contact the relatively steeper ramps 946 of each of the first jaw member 834 and the second jaw member 836, which can result in relatively quick movement of the first jaw member 834 and the second jaw member 836 toward each other. As the user continues to slide the actuator 818 distally, the distal end 814 of the second elongated body 812 can slide along the relatively shallower ramps 948 of each of the first jaw member 834 and the second jaw member 836. This can result in a more gradual closure of the first jaw member 834 and the second jaw member 836.

During the distal movement of the actuator 818, the distal tooth 964 of the locking device 844, can engage the ratchet teeth 976 and the ratchet teeth 978, such that the user can lock the actuator 818 in a predetermined number of positions. When a "hard stop" is reached, for example, when the first jaw member 834 and the second jaw member 836 contact a needle, or other tool to be grasped, further movement of the second elongated body 812 in the distal direction can be prevented. The distance that the second elongated body 812 moves in the distal direction 820 can be less than the distance that the biasing shaft 904 moves distally, due to the compressibility of the proximal biasing member 920, and since the pin 916, which secures the actuator 818 to the biasing shaft 904, can move proximally and distally within the intermediate slot 815 defined by the second elongated body 812. As a result, the proximal biasing member 920 can continue to exert a force acting in the distal direction 820 on the second elongated body 812. This, in turn, can result in a clamping force being exerted by the first jaw member 834 and the second jaw member 836 on the needle, or other tool, which can prevent the needle, or other tool, from being inadvertently released. In the absence of this biasing force exerted by the proximal biasing member 920, the clamping force may not be maintained since a gap between the distal tooth 964 of the locking device 844 and the ratchet teeth 976 and 978 can occur, when the distal tooth 964 snaps into position between adjacent ones of the ratchet teeth 976 and adjacent ones of the ratchet teeth 978, as the actuator is locked.

Use of the needle drivers disclosed herein can result in various advantages. For example, the ergonomic shape of a first elongated body (e.g., 602, 802) of a needle driver (e.g., 600, 800) can allow a healthcare provider to comfortably grasp the needle driver (e.g., 600, 800) and to easily and efficiently manipulate it during a surgical procedure. Digit receivers (e.g., 668, 868) of the needle drivers (e.g., 600, 800), as well as the protrusion 952 of the first elongated body 802 of needle driver 800, can enhance this ability.

The configuration of the locking devices (e.g., 644, 844) of the needle drivers (e.g., 600, 800), and the configuration of the mating ratchet teeth (e.g., 642 of needle driver 600, and 956, 958 of needle driver 800), allow the respective actuators (e.g., 618, 818) to be locked in a predetermined number of positions, and provide tactile feedback to the healthcare provider. The convenient location and configuration of the lock release members (e.g., 652, 970) of the needle drivers (e.g., 600, 800), allow the user to conveniently unlock the respective actuator (e.g., 618, 818).

The configurations and series arrangement of the proximal and distal biasing members (e.g., 620, 618; 920, 918) of the needle drivers (e.g., 600, 800) can permit continuous clamping force to be applied to the needle, or other tool being manipulated, even after the respective actuator (e.g., 618, 818) has been locked in one of a predetermined number of positions, which can prevent the needle, or other tool, from being inadvertently released. The use of the relatively shallower ramps (e.g., 748, 948) of the jaw members (e.g., 634, 636; 834, 836) of the needle drivers (e.g., 600, 800) can provide a mechanical advantage, which can provide a relatively greater clamp force, for a given force applied to an actuator (e.g., 618, 818) by a healthcare provider, which can reduce fatigue of the healthcare provider.

Use of cam members (e.g., 760, 762; 960, 962) can bias the corresponding jaw members to the open position, which can facilitate releasing the needle or other tool. The arrangement and combined spring constant of the proximal and distal biasing members (e.g., 720, 718; 920, 918) can facilitate retracting the second elongated body (e.g., 612, 812) of the needle driver (e.g., 600, 800), which can further facilitate opening the respective jaw members and the releasing the needle, or other tool.

While the present invention has been illustrated by the description of embodiments thereof, and while the embodiments have been described in considerable detail, it is not intended to restrict or in any way limit the scope of the appended claims to such detail. Additional advantages and modifications will be readily apparent to those skilled in the art. The invention is therefore not limited to the specific details, representative apparatus and method, and illustrated examples shown and described. Accordingly, departures may be made from such details without departing from the scope or spirit of the invention.

What is claimed is:

1. A needle driver, comprising:
 a first elongated body comprising a distal end and a proximal end, the first elongated body defining an interior chamber;
 a second elongated body comprising a distal end and a proximal end, the second elongated body defining an interior space, the second elongated body being slideable within the interior chamber defined by the first elongated body, between a retracted position and an extended position;
 a clamping device comprising a clamping end and a connecting member, the connecting member being affixed to the first elongated body and coupled with the clamping end;
 a biasing shaft slideably disposed within the interior space defined by the second elongated body;
 an actuator affixed to the biasing shaft, the actuator being slideable in a proximal direction and a distal direction; and
 a proximal biasing member, the proximal biasing member extending between the biasing shaft and the second elongated body.

2. The needle driver of claim 1, wherein:
the proximal end of the second elongated body comprises a proximal flange, and the biasing shaft comprises a proximal flange;
the proximal biasing member is disposed between the proximal flange of the second elongated body and the proximal flange of the biasing shaft.

3. The needle driver of claim 2, further comprising:
a distal biasing member; and
an alignment pin; wherein
the biasing shaft defines a slot, and the second elongated body defines a proximal slot;
the alignment pin is affixed to the first elongated body and extends through each of the proximal slot defined by the second elongated body and the slot defined by the biasing shaft; and
the distal biasing member is compressed between the alignment pin and the proximal flange of the second elongated body.

4. The needle driver of claim 3, further comprising:
a guide pin;
the second elongated body further defines an intermediate slot;
the guide pin extends through the intermediate slot defined by the second elongated body and is secured to each one of the actuator and the biasing shaft, the guide pin being slideable within the intermediate slot, the biasing shaft being movable with the actuator proximally and distally.

5. The needle driver of claim 3, wherein:
each of the proximal biasing member and the distal biasing member comprises a compression coil spring having a spring constant, the spring constant of the proximal compression coil spring being greater than the spring constant of the distal compression coil spring.

6. The needle driver of claim 5, wherein:
the proximal compression coil spring and the distal compression coil spring are disposed in a series relationship with each other.

7. The needle driver of claim 6, wherein:
the proximal compression coil spring applies a force, in a distal direction, to the second elongated body as the actuator slides distally, and continues to apply a force, in a distal direction, to the second elongated body after movement of the actuator has stopped.

8. The needle driver of claim 1, further comprising:
a connector; wherein
the second elongated body defines a distal slot;
the connector extends through the distal slot defined by the second elongated body and is secured to each of the first elongated body and the connecting member of the clamping device.

9. The needle driver of claim 1, wherein:
the clamping end of the clamping device comprises a first jaw member and a second jaw member opposing the first jaw member;
each one of the first jaw member and the second jaw member is pivotally coupled with the connecting member of the clamping device, and is pivotable between an open position and a closed position; and
each of the first jaw member and the second jaw member is in the open position when the second elongated body is in the retracted position and moves toward the closed position as the second elongated body slides distally toward the extended position.

10. The needle driver of claim 9, wherein:
the first jaw member comprises a relatively steeper ramp and a relatively shallower ramp extending distally from the relatively steeper ramp;
the second jaw member comprises a relatively steeper ramp and a relatively shallower ramp extending distally from the relatively steeper ramp; and
the distal end of the second elongated body initially contacts the relatively steeper ramp of the first jaw member and the relatively steeper ramp of the second jaw member, and then contacts the relatively shallower ramp of the first jaw member and the relatively shallower ramp of the second jaw member, forcing each of the first jaw member and the second jaw member toward a respective closed position, as the second elongated body is extended.

11. The needle driver of claim 10, wherein:
the connecting member of the clamping device comprises a proximal end and a distal end;
the proximal end of the connecting member is affixed to the first elongated body;
each of the first jaw member and the second jaw member is pivotally coupled with the distal end of the connecting member.

12. The needle driver of claim 11, wherein:
the clamping device further comprises a first arm and a second arm;
the first arm pivotally couples the first jaw member with the distal end of the connecting member; and
the second arm pivotally couples the second jaw member with the distal end of the connecting member.

13. The needle driver of claim 12, further comprising:
a first cam member and a second cam member, each of the first cam member and the second cam member being secured to the second elongated body and extending into the interior space defined by the second elongated body; wherein
the first cam member contacts the first arm as the second elongated body is retracted, biasing the first jaw member toward the open position; and
the second cam member contacts the second arm as the second elongated body is retracted, biasing the second jaw member toward the open position.

14. The needle driver of claim 13, wherein:
each of the first cam member and the second cam member comprises a pin.

15. The needle driver of claim 1, further comprising:
a locking device attached to the actuator, the locking device being movable with the actuator proximally and distally; wherein
the first elongated body comprises at least a first plurality of ratchet teeth extending inwardly from the distal end of the first elongated body; and
the locking device is configured for selective engagement with the first plurality of ratchet teeth.

16. The needle driver of claim 15, further comprising:
a lock release member coupled with the actuator; wherein
the lock release member is operable for selectively disengaging the locking device from the first plurality of ratchet teeth to unlock the actuator.

17. The needle driver of claim 16, wherein:
the lock release member comprises a button movably coupled with the actuator.

18. The needle driver of claim 16, wherein:
the lock release member comprises a lever pivotally coupled with the actuator.

19. The needle driver of claim 16, wherein:
the first elongated body further comprises a second plurality of ratchet teeth laterally spaced from the first plurality of ratchet teeth;
the locking device extends distally away from the actuator and comprises a distal tooth;
the distal tooth is configured to engage the first plurality of teeth and the second plurality of teeth to selectively lock the actuator in a predetermined number of positions; and
the lock release member is operable for selectively disengaging the distal tooth of the locking device from the first plurality of ratchet teeth and the second plurality of ratchet teeth to unlock the actuator.

20. A needle driver, comprising:
a first elongated body comprising a distal end and a proximal end, the first elongated body defining an interior chamber;
a second elongated body comprising a distal end and a proximal end, the second elongated body defining an interior space, the second elongated body being slideable within the interior chamber defined by the first elongated body, between a retracted position and an extended position;
a clamping device comprising a first jaw member, a second jaw member, a first arm, a second arm, and a connecting member, the connecting member being affixed to the first elongated body;
a biasing shaft slideably disposed within the interior space defined by the second elongated body;
an actuator affixed to the biasing shaft, the actuator being slideable in a proximal direction and a distal direction; and
a first cam member and a second cam member, each of the first cam member and the second cam member being secured to the second elongated body and extending into the interior space defined by the second elongated body; wherein
the first arm of the clamping device pivotally couples the first jaw member with the connecting member and the second arm of the clamping device pivotally couples the second jaw member with the connecting member;
the first cam member contacts the first arm as the second elongated body is retracted, biasing the first jaw member toward the open position; and
the second cam member contacts the second arm as the second elongated body is retracted, biasing the second jaw member toward the open position.

21. The needle driver of claim 20, further comprising:
a proximal compression coil spring;
a distal compression coil spring; and
an alignment pin; wherein
the proximal compression coil spring extends between the biasing shaft and the second elongated body;
the biasing shaft defines a slot, and the second elongated body defines a proximal slot;
the alignment pin is affixed to the first elongated body and extends through each of the proximal slot defined by the second elongated body and the slot defined by the biasing shaft; and
the distal compression coil spring is compressed between the alignment pin and the proximal flange of the biasing shaft.

22. The needle driver of claim 21, wherein:
each of the proximal compression coil spring and the distal compression coil spring has a spring constant, the spring constant of the proximal compression coil spring being greater than the spring constant of the distal compression coil spring; and
the proximal compression coil spring and the distal compression coil spring are disposed in a series relationship.

23. A needle driver, comprising:
a first elongated body comprising a distal end and a proximal end, the first elongated body defining an interior chamber;
a second elongated body comprising a distal end and a proximal end, the second elongated body defining an interior space, the second elongated body being slideable within the interior chamber defined by the first elongated body, between a retracted position and an extended position;
a clamping device comprising a clamping end and a connecting member, the connecting member being affixed to the first elongated body and coupled with the clamping end;
a biasing shaft slideably disposed within the interior space defined by the second elongated body;
an actuator affixed to the biasing shaft, the actuator being slideable in a proximal direction and a distal direction;
a proximal biasing member, the proximal biasing member extending between the biasing shaft and the second elongated body;
a locking device attached to the actuator, the locking device being movable with the actuator proximally and distally; and
a lock release member coupled with the actuator; wherein the first elongated body comprises at least a first plurality of ratchet teeth extending inwardly from the distal end of the first elongated body into the interior chamber defined by the first elongated body;
the locking device is configured for selective engagement with the first plurality of ratchet teeth to releasably lock the actuator; and
the lock release member is operable for selectively disengaging the locking device from the first plurality of ratchet teeth.

24. The needle driver of claim 23, wherein:
the proximal end of the second elongated body comprises a proximal flange, and the biasing shaft comprises a proximal flange; and
the proximal biasing member is disposed between the proximal flange of the second elongated body and the proximal flange of the biasing shaft.

25. The needle driver of claim 24, wherein:
a distal biasing member; and
an alignment pin; wherein
the biasing shaft defines a slot, and the second elongated body defines a proximal slot;
the alignment pin is affixed to the first elongated body and extends through each of the proximal slot defined by the second elongated body and the slot defined by the biasing shaft; and
the distal biasing member is compressed between the alignment pin and the proximal flange of the biasing shaft.

26. The needle driver of claim 25, wherein:
the lock release member comprises a button movably coupled with the actuator.

27. The needle driver of claim 25, wherein:
the lock release member comprises a lever pivotally coupled with the actuator.

28. The needle driver of claim 25, wherein:
the first elongated body further comprises a second plurality of ratchet teeth laterally spaced from the first plurality of ratchet teeth and extending inwardly from the distal end of the first elongated body into the interior chamber defined by the first elongated body;
the locking device extends distally away from the actuator and comprises a distal tooth;
the distal tooth is configured to engage the first plurality of ratchet teeth and the second plurality of ratchet teeth to selectively lock the actuator in a predetermined number of positions; and
the lock release member is operable for selectively disengaging the distal tooth of the locking device from the first plurality of ratchet teeth and the second plurality of ratchet teeth to unlock the actuator.

* * * * *